(12) United States Patent
Abdullah et al.

(10) Patent No.: US 7,732,669 B2
(45) Date of Patent: *Jun. 8, 2010

(54) REGULATORY SEQUENCES FOR REGULATION OF GENE EXPRESSION IN PLANTS AND OTHER ORGANISMS, AND COMPOSITIONS, PRODUCTS AND METHODS RELATED THERETO

(75) Inventors: Siti Nor Akmar Abdullah, Selangor (MY); Zubaidah Ramli, Selangor (MY)

(73) Assignee: Malaysian Palm Oil Board, Kajang, Selangor (MY)

( * ) Notice: Subject to any disclaimer, the term of this patent is extended or adjusted under 35 U.S.C. 154(b) by 513 days.

This patent is subject to a terminal disclaimer.

(21) Appl. No.: 11/635,790

(22) Filed: Dec. 8, 2006

(65) Prior Publication Data

US 2007/0238890 A1 Oct. 11, 2007

Related U.S. Application Data

(62) Division of application No. 10/141,773, filed on May 10, 2002, now Pat. No. 7,173,120.

(30) Foreign Application Priority Data

Mar. 29, 2002 (MY) ............................... PI 20021165

(51) Int. Cl.
*A01H 5/00* (2006.01)
*C12N 15/82* (2006.01)
*C07H 21/04* (2006.01)

(52) U.S. Cl. ..................... 800/298; 800/287; 536/24.1
(58) Field of Classification Search ....................... None
See application file for complete search history.

(56) References Cited

OTHER PUBLICATIONS

Database GenEMBL Accession AJ236913, Abdullah, S.N.A., Aug. 11, 1999.*

* cited by examiner

*Primary Examiner*—Elizabeth F McElwain
(74) *Attorney, Agent, or Firm*—Morgan Lewis & Bockius LLP

(57) ABSTRACT

The invention relates to regulatory sequences that regulate gene expression in the mesocarp and/or senescent leaves of certain plants. In certain embodiments, the invention is directed to abundant and selective expression of type 3 metallothionein-like genes in the mesocarp of a variety of plants including members of the Palme family. The invention also relates to methods of generating transgenic plants and plant tissues that comprise a nucleic acid of the invention. The invention further provides products derived from transgenic plants, plant materials or plant cells of the invention. Particular applications in oil palms are discussed. The invention further relates to nucleic acid constructs of the invention in cells of organisms other than plants.

9 Claims, 19 Drawing Sheets

```
aacattgtctttggtttcctgcttcgaaactcaaaacATGTCGACCTGCGGCAACTGCGA        60
                                      M  S  T  C  G  N  C  D
TTGTGCTGACAAGAGCCAGTGTGTGAAGAAGGGAAACAGCTACGGCATCGAGATCATCGA       120
 C  A  D  K  S  Q  C  V  K  K  G  N  S  Y  G  I  E  I  I  E
GACCGAAAAGAGCAACTTCAACAATGTCATCGATGCCCCGGCTGCTGCTGAGCACGAGGG       180
 T  E  K  S  N  F  N  N  V  I  D  A  P  A  A  A  E  H  E  G
CAACTGCAAGTGTGGTGCTAGCTGTGCTTGTGTGGATTGCAAGTGTGGCCAATGAgcaac       240
 N  C  K  C  G  A  S  C  A  C  V  D  C  K  C  G  Q  *
atctatgagcactatagcaaacaagaaaagaaagagatatgtgtgatatgggtatgttgg       300
actaaataattctggatatgtttctgtcatggtgtgttattgtagcaaggatgtgtgtctg     360
tcatggtgtgttattgttgtaaggttggaggaagacaatatctgggcttccttatccagt       420
ttcgcactaatttctattaacctggttctaattaatggattgctattggtagaaaaaaaa      480
aaaaaaaaa                                                          490
```

Fig. 1a  The nucleotide and deduced amino acid sequences of pOPSN6. The ORF is capitalised and the UTR are in lower case. The consensus sequences for translation start and polyadenylation signal are doubly underlined. The amino acids are shown in single letter codes.

AACGTATTGGGTGATCGAATCTATCAGAGTTACAAACATTGTCTTTGGTT     50
5' extension to the original cDNA sequence of pOPSN6

TCCTGCTTCGAAACTCAAAACATGTCGACCTGCGGCAACTGCGATTGTGC     100

TGACAAGAGCCAGTGTGTGAAGAAGGGAAACAGCTACGGCATCGAGATCA     150

TCGAGACCGAAAAGAGCAACTTCAACAATGTCATCGATGCCCCGGCTGCT     200

GCTGAGCACGAGGGCAACTGCAAGTGTGGTGCTAGCTGTGCTTGTGTGGA     250

TTGCAAGTGTGGCCAATGAGCAACATCTATGAGCACTATAGCAAACAAGA     300

AAAGAAAGAGATATGTGTGATATGGGTATGTTGGACTAAATAATTTG<u>GAT</u>     350
                                                                Complementary
<u>ATGTTTCTGTCATGGTG</u>     400
sequence to the nested primer

Fig. 1 b    The nucleotide sequence of the cloned 5' – RACE product. The 5' extension to the original cDNA sequence of pOPSN6 and the complementary sequence to the nested primer used in the secondary PCR reaction are bold and underlined.

A) Alignment between deduced amino acid sequences of pOPSN6 (MT3-A) and pOPSN7 (MT3-B)

This alignment was performed with the 'gap' GCG program. Identical amino acids are shown with matching lines while similar amino acids are indicated by single or double dots. The sequences are found to be 70% identical and 86% similar over the entire length of both proteins.

```
MT3-A  MSTCGNCDCADKSQCVKKGNSYGIEIIETEKSNFNNVIDAPAAAEHEGNC  50
       |||||:|||||||||||||:||: |||||||  |::|::..:||||.:   |
MT3-B  MSTCGDCDCADKSQCVKKGNGYGMVIIETEKSYFEEVVEVAAAAEPD..C  48

KCGASCACVDCKCGQ*  66
       |||..|||.:|.||.|
       KCGSNCACAGCTCGK*  64
```

B) Table summarising percentages of identity at the nucleotide and amino acid levels between sequences of pOPSN6 and pOPSN7

| | 3'-UTR | 5'-UTR | coding nucleotides | amino acids |
|---|---|---|---|---|
| identity (%) | 47 | 41 | 78 | 70 |

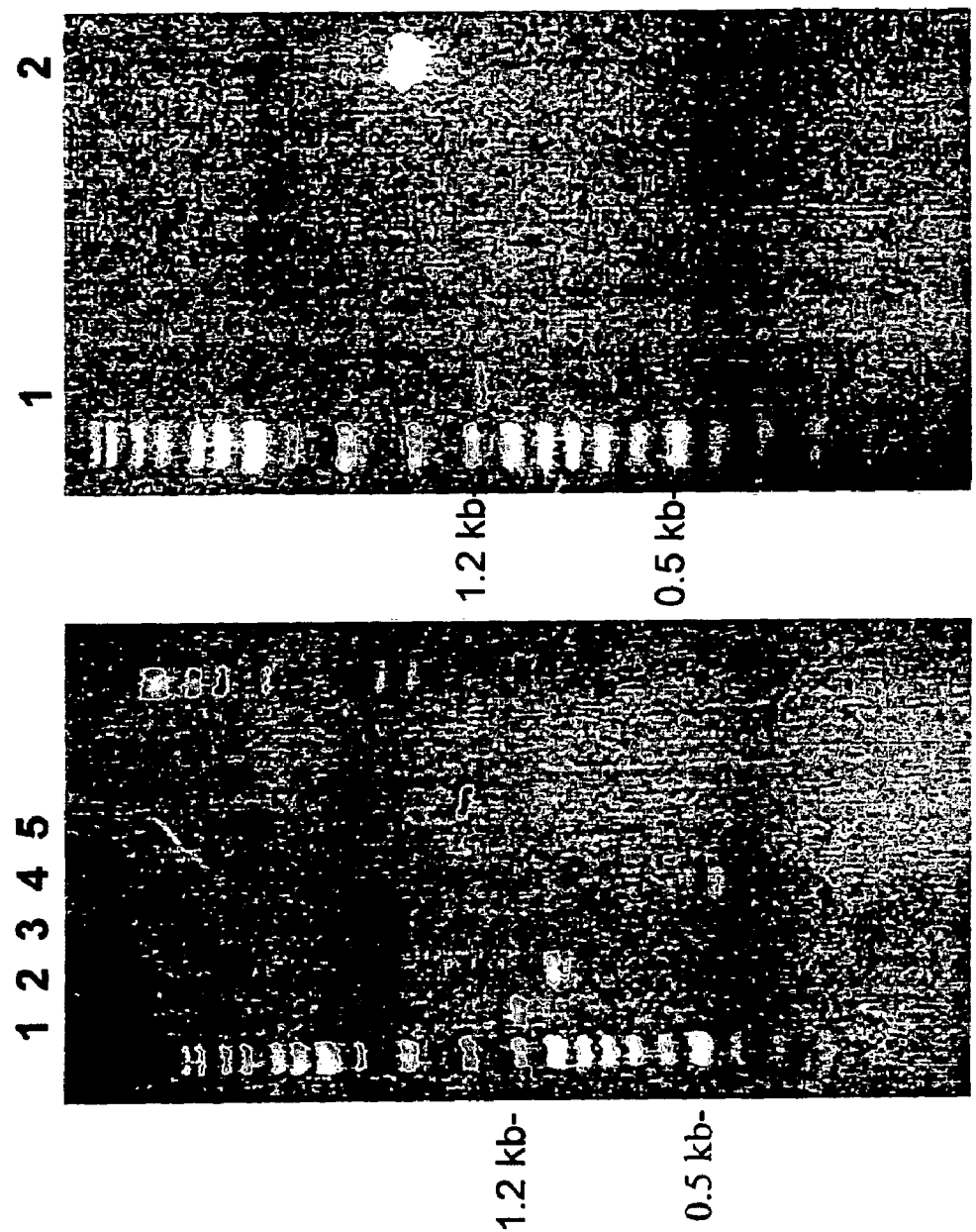

| | |
|---|---|
| GCCCTTACTATAGGGCACGCGTGGTCGACGGCCCGGGCTGGTAAAATTACTGCCATGGAG | 60 |
| GGTCACAATGATGCAACTAAACATGATAATCTCATCACCTCCATCTACATCATCTTTAAT | 120 |
| CCTACATGAATCATTCCATATCAAATACCTCCCAACTAAAATCGAACCCCATCTTCTTGT | 180 |
| CCAAGTGACAAAGAATGATACCATGGAGGCAAGCATTTAACCAGAACTAGAAGTCTGCCA | 240 |
| AGGAGTAGTTGACAGAATCGAACCCCATCTTATTGTCCACCATTCTTGACACAAAAATAA | 300 |
| CCCGTGCAGATAGACTATAGTCAATCGTTATCCAAGTCCACATGAACTCTGCCAAGGAGT | 360 |
| AGTTGGTTTTACTTACAAATTTTGGTTATCTTTATAAACATTTTGTAAGGTGTAGGATTT | 420 |
| GTGTGATAACATTTTGATTAGTTAGGCTAAAAATTGTATGTGCTGAGCTACGATACCTTC | 480 |
| TTTCTGGTAGAAAGCTACGATACCTTTAACCAGAAAAGGATCCAAAGAAACGAACGAAAC | 540 |
| CAAACTAGGGGCTAACTCCAAAGTAGGCGAAGCTAGAAAAGACTCGACTTCTCTGTACCC | 600 |
| CAGAAGATTGCAAGGCAATTTCTCTCCACAAAAACAAAAGAACCACGAAGCAAACAAAGC | 660 |
| AAAACCAAGCAAATTTCCTTCCAATTTGCGTCACCGGGTTATCTCCACGCA<u>TTAGAATTT</u> <br> ERE-reverse | 720 |
| TGAATCGATCTCCATCAAACGTCACGACAGACAAAGAAGACGACTTGACTAGCACTGTAC | 780 |
| CAAGAATGTGTGACGTGGCAGCTTGCGTGTGCCAGCGGTATGGTCTTCAGCCAGGAAGAA | 840 |
| AAAGAGGGAGATATGACAAGAGAGGCTTGTGGGAAATCACACACCCATTATTGAGATTCC | 900 |
| TTCCGGATTATTCGTCTAGAGGCGTGTGCACGGCGCTGAGAAGCGTGTGGGCTCTGCGAA | 960 |
| TTACCAAGCTAGCCTCTCATGGCCAAGTAAATGCC<u>TATAAAT</u>GCCCATCGCCTCCGCCCT <br> TATA box | 1020 |
| TCCTCAAC<u>A</u>ACGTATTGGGTGATCGAATCTATCAGAGTTACAAACATTGTCTCTGGTTTC <br> Transcriptional start | 1080 |
| CTGCTTCGAAACTCAAAAC<u>ATG</u>TCGACCTGCGGCAACTGCGATTGTGCTGACAAGAGCCA <br> Translational start | 1140 |

Fig. 9 The nucleotide sequence of pMT3A-P1a. The putative ethylene responsive element (ERE-reverse), TATA box, the adenine at the 5' end of the cloned 5' RACE (likely transcription start site) and the ATG codon for start of translation are bold and underlined.

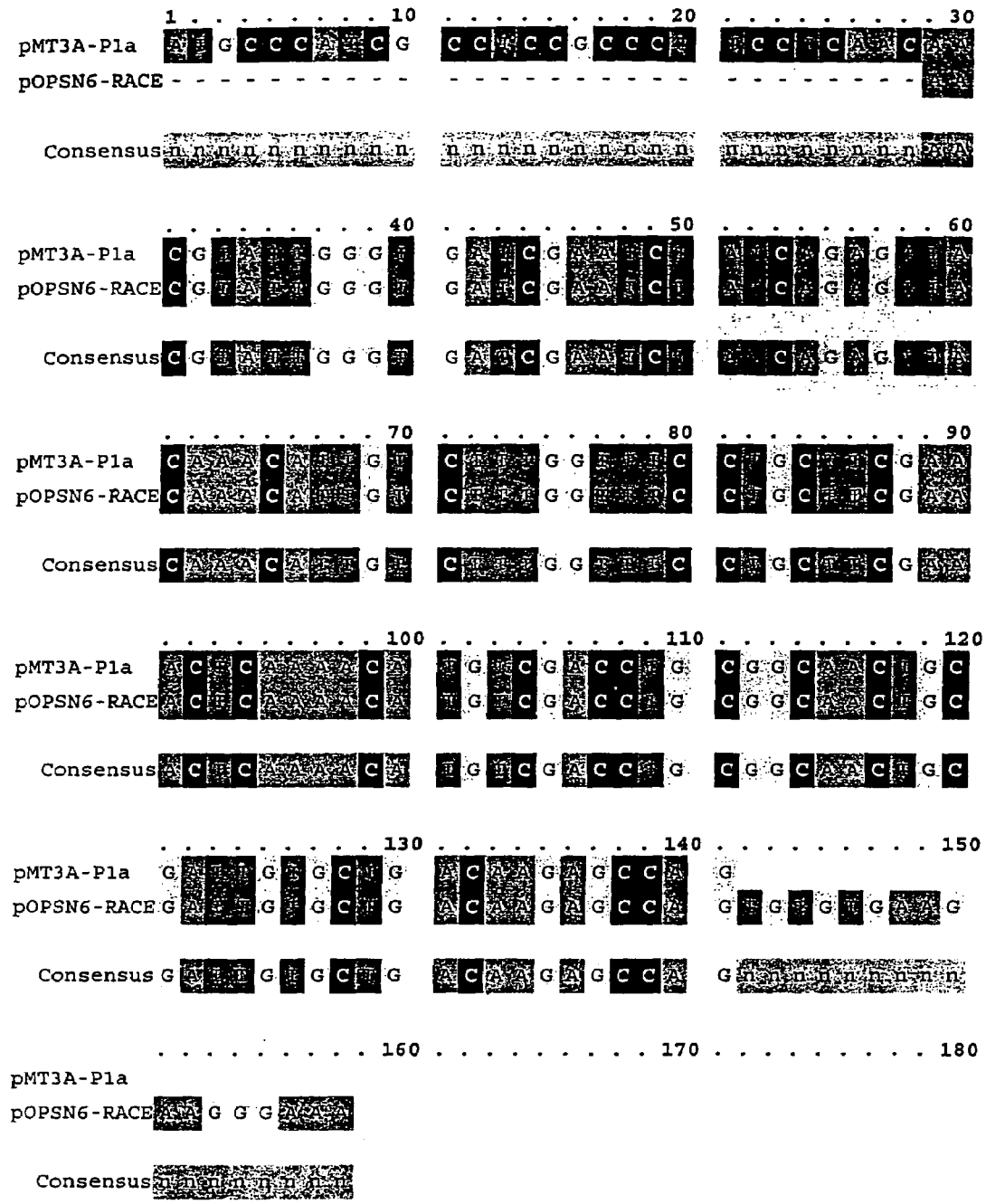
Fig. 10    DNA sequence alignment of pMT3A-P1a (3'– end of nucleotide 1000) and sequence of the 5' RACE product (nucleotide 1 to nucleotide 131) clearly showing 100% homology within the overlapping region.

Figure 12 GFP expression in mesocarp and leaf tissues bombarded with HBT1-α

| Helium Pressure (Psi) | No. of green spots after 2 days in culture | |
|---|---|---|
| | Mesocarp (target tissues) | Leaf (control tissues) |
| 900 | 1 | 10 |
| 1100 | 10 | 33 |
| 1350 | 20 | 45 |
| 1550 | 87 | 6 |
| 1800 | 10 | 1 |

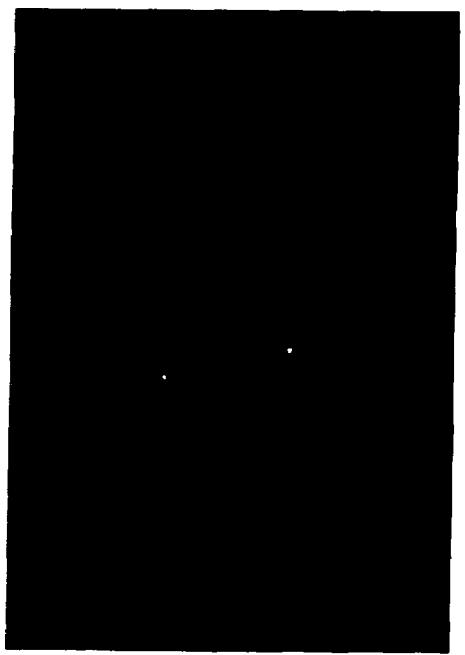
Mesocarp slices bombarded with MT3AP-EGFP
Leaf tissues bombarded with MT3AP-EGFP
Figure 13

MESOCARP
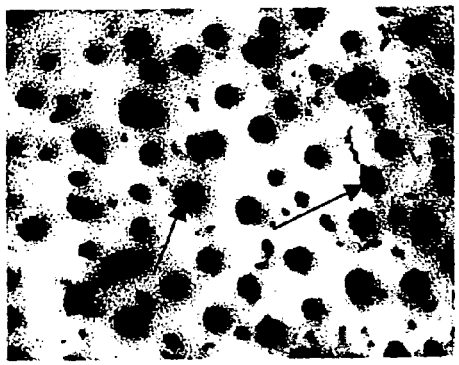
Constitutive promoter (6.6x)
LEAF
Constitutive promoter (10.0x)
MT3-A promoter (8.0x)
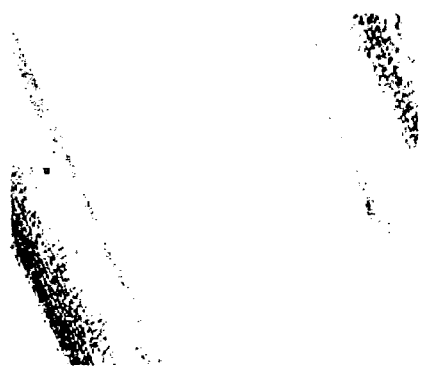
MT3-A promoter (8.0x)
FIGURE 14

```
atgtcgacctgcggcgactgcgactgcgctgacaagagccagtgcgtgaagaagggaaat  60
 M  S  T  C  G  D  C  D  C  A  D  K  S  Q  C  V  K  K  G  N
ggttacggcatggtcatcatcgagactgaaaagagctacttcgaggaagtcgttgaggtg 120
 G  Y  G  M  V  I  I  E  T  E  K  S  Y  F  E  E  V  V  E  V
gcagcagccgcggagcctgactgcaaatgcggctctaactgcgcctgcgctggttgcacc 180
 A  A  A  A  E  P  D  C  K  C  G  S  N  C  A  C  A  G  C  T
tgtggcaaatga                                                 192
 C  G  K  *
```

Fig. 15 Coding Sequence for MT3-B

Fig.16 Genomic Sequence for MT3-B (AJ236914)

```
   1  tggactcagt tcagaactaa taccaaaatg agccaacgtt gaggtagctg atgaaggaga
  61  aatttcggac gcttttgatg ttcagctaga aaaatcttac tagtaaagag gggaaaacca
 121  aaatcggcaa cctttttttt ttggtagaaa aatcagcaac ctttcaataa agagtttaa
 181  tcctgtaaaa tatcaagtct agcaaattac caaagtaaag tgttgaaaaa aattaaaaaa
 241  aaaaaaaggg aatccgatct tccacaacct tatagcattc cagctaatgc ggctatccaa
 301  aataagatgg atgggatgca ccagtcattc tgatgtgctt agaatttcca tcaaactcta
 361  tcgtgcaact tgtgatttga caattcagag gtcgatgggg cagtgtcacc tttcatcatg
 421  cacgcaagaa tccggggccc ttgcgagagt atttgcatgt taagcaaacg ttaaaaataa
 481  agggatttga catcagaagc tcatagccct cctaccaaaa aaagagagag agaaacttca
 541  accctccatt attgagattc catttggata gttttggtcg aggcgtgtgc cgccactgta
 601  gcgtcagtaa tccgtttaag cccaccctcg ctttcctcat ccttgaaaac gcctataaat
 661  atgggcggca cccaagcctc tttcctcaca gccagaccca gcaaaccttc tctcgagtca
 721  cctgccatcc cttcgtccct cctctccttt ttagcgacgc accatgtcga cctgcggcga
 781  ctgcgactgc gctgacaaga gccagtgcgt gtaagtagtc cctcaccttg gaagctctcg
 841  ctaacgcata gcagtcatgt tgcaaaactt atggttttta ctactaccag tcatcttgag
 901  gagaaattat tagatggacc atgatgcatc atggatctaa aatgaaataa atcattttt
 961  tcttttcct tatatgtaat agcagcatgt attagaatga tttcaccta ggtccattgg
1021  gatctagtcc acctaattaa taatttctcc atatttgcct ttggccttg gtcatgatga
1081  ctggcatgtt tacaaattca gcatctctat tttactatct agaagatttt tcttatcaaa
1141  tgatcaatat tttaagtttt taatttcaac taagtagtta atgttgtggg gggttctggc
1201  ttatatggaa tgcgatcttt tttttctcat gagtcgtctt taaaggaca aaattataaa
1261  gccctgtgcc ataagtcaga gaccgaagtg gacaatatct catgcatgtt ggagtggaga
1321  ctgatccatc caagtcatga gcccttgacc gcaacattcg tgtcatctgt gagataccaa
1381  tattgtgggg gattctggct tatatgaaat gtgatcttct ttttctcatg aggcgcctta
1441  taaaaagcaa aactgtgaag ccctatgtca taagccagag gtcaaatgg acaatatctc
1501  atatatgtta gagtgaagac tgatctatcc gagtcatgag ctccttgaccg caatattcat
1561  gttatttgtg ggataccgtc tcctactcac acacagcact cctttttgat tgggaggcta
1621  atattgtggg ggaaaaacgt attattagtc ccatatcgat tgtgagttaa gagaaaatct
1681  ggtttatatg gaatgggacc ttctctcttc cgtgagatgc tttttaaagg acaaaactgt
1741  aagatcccat gccatgagct agagatcgaa gtggataata cctcacacat gcaggagcgg
1801  agaccgatcc attccaacca caaatctttg accacaacgc ttagaagtga ttttatcagc
1861  ctctctcttg ctgtaggtaa ataatacatg taacaaattt caaacctcct aagtatacca
1921  catcagagtt tgatactaac ttttgtggtg catgcttact aaatagtcta actagatgag
1981  ggtacttcta ttattttat gtcatctact aaactttatt gcccattctg atctaaatgg
2041  tttagaggag gtggtgtaac tttaaatttt ggaattttgg cacataaacc cacgtaaaac
2101  cgcactgacc tggggtagaa ctttaaaatc actagaatga agggggggaa aaacaaaga
2161  acttgtgtta gctagcttct atttatatat ttttctcata agaaaagctc actaagctaa
2221  cgaatctatt tgacgactgc aggaagaagg gaaatggtta cggcatggtc atcatcgaga
2281  ctgaaaagag gtatcaatca gatccaacaa gaaaataata ataacaatta aaaaaagaca
2341  ttttgtgccc atcggtgtat ggtatgcatg tacatacgta cgtatatatg tatacatata
2401  tgtgtgcata ttagtagaag atattaataa aaaacactc aaatttggct catgatgcac
2461  agaaacctgt tctaaagttt ttttcttat tttttttttt ttttttttg ttgggttggg
2521  ggcggcgggg tggggtaccc taaagacttt atttcagggc aattcctaat gtattggact
2581  gaatcatttg ttgcagctac ttcgaggaag tcgttgaggt ggcagcagcc gcggagcctg
2641  actgcaaatg cggctctaac tgcgcctgcg ctggttgcac ctgtggcaaa tgatagccta
2701  tctgctataa ttgttactat gtaagcaagg gaagataaaa tgacactagg gtttggttgt
2761  ggcaagtgat gtaggagtgc cattctatgt agtggtacca aggctgggag taagctgatg
2821  tccagctatc tcaacctaag taatatgtct gtgtcctatc ctgttttaacg gacttgtact
2881  aaaataaaat ctggctttgg tttgagtagt gatttctatg tctttttccac agtgtgaagt
2941  tttttttttt ttttgagtaa aataatgtga agtggtggtg ctgcatttta accttacatg
3001  ctccaggagc aactaaatct aagtagtagg tgcaaactga gcttagccca aagatttcac
3061  ctctcatatt tgggatctgg gagatcctgt cttcagtaca ccttgacatg agtactttca
3121  ttattttgtt cccactatgc tcaaaagata atatagacat atgcacacat acatatacaa
3181  atacatacat atatacctac atacatatac acatgtacca tgtggcacaa ggggattagt
```

```
3241 gtgtcgtaga gacctgacgg aatacctgta ctacaagagt tccaacctag tacgctggcc
3301 ttagaataaa agagcactca atctcatggg attccgcttg gtgtttttaa tctacctttc
3361 ttcgtgacca actcccacgg atggtaatac gatgtatcag atcaaagatc cattgctcca
3421 accatgcgaa ccatcaacca ctgaccatgc caactgtaat tcacgttatg aaatactatt
3481 tgcctcaatc atgcgagtac ctttttttcg gttcgtgata tttttaagaa gatatttagt
3541 ttgtgtagga atgagaatga gaattaaaat gatttggaat cgaaatcgga atagtcaaat
3601 cctacaaaat gtttgatttg tgaccggaat cgaaatcaga attggaataa aaatttgaat
3661 ccatagaaac gagtagggat tgaattccat atagattgag ccatttccat tccacctgta
3721 atcggaatca gaatcggaat gagaatcttt ctaaccaaac agctggaatg gaagtcaccc
3781 atttcgattc cgatttcaga cctccattct ctccaactaa acacccctta agttctttgc
3841 tttctatttc ctcactcttc atcataaagt atagtatttt cgcattgctt tcgttcttta
3901 ttttcatttt caagaacgaa tcaaggacaa gattga
```

REGULATORY SEQUENCES FOR REGULATION OF GENE EXPRESSION IN PLANTS AND OTHER ORGANISMS, AND COMPOSITIONS, PRODUCTS AND METHODS RELATED THERETO

CROSS-REFERENCE TO RELATED APPLICATIONS

The present application is a divisional application of U.S. application Ser. No. 10/141,773, filed May 10, 2002, which has issued as U.S. Pat. No. 7,173,120, and which claims the benefit of Malaysian Patent Application No PI 20021165, filed Mar. 29, 2002, each of which is incorporated by reference in their entirety.

BACKGROUND OF THE INVENTION

The fatty acid composition of vegetable oils determines their physical and chemical properties and hence their applications. The wide range of applications of vegetable oils, 90% edible and 10% non-edible, reflects their fatty acid compositional diversity. Vegetable oils are a renewable resource that can serve as feedstock to produce environmental friendly industrial products such as lubricants, paints, detergents and body care. Demand for these oils in the non-food sector is likely to increase in response to the shrinking reserves of mineral oils.

Hundreds of different fatty acids have been identified and characterised in the plant kingdom, but most of them are not available for economic uses. Genetic engineering provides the means to tap these vast resources by producing fatty acids of economic importance in the storage lipids of oil crops. Achievements through breeding alone or in combination with mutagenesis, such as in the development of rapeseed oil with low content of erucic acid (22:1) and sunflower oil with high level of oleic acid, indicate that plants can tolerate a wide variation in fatty acid composition of storage lipids.

Palm oil is generally extracted from the mesocarp of the oil palm fruits. Palm oil which contains about 50% saturated, 40% monounsaturated, 10% polyunsaturated fatty acids is a semi-solid fat at room temperature. Its fatty acid composition consists of 44% palmitic acid (16:0), 5% stearic acid (18:0), 39% oleic acid (18:1) and 10% linoleic acid (18:2). Palm oil products are primarily used in the food sector, typically as solid fat for margarine, shortening and cooking oil production. Non-edible or technical applications are, however, substantial and increasing. These include, for example, soap, oleochemical-production and use as an energy source for cars.

Production of novel high-value products by genetic engineering provides the opportunity to diversify the use and to increase the economic value of palm oil. Production of specialty oils for industrial applications would be a very attractive proposition for the oil palm, since it is the most productive of oil crops. Recombinant DNA technology has been used successfully to manipulate fatty acid biosynthetic pathways in a variety of transgenic oil crops, such as rapeseed, to produce a modified oil composition. Reported success in raising the levels of lauric acid and stearic acid in rapeseed oil proved that both fatty acid chain length and the level of fatty acid unsaturation can be modified.

Genetic engineering efforts rely heavily on the availability of a reliable transformation technique for achieving stable integration and a regulatory sequence for controlling expression of introduced genes. With oil palms, there has been significant progress in the development of a reliable transformation system using biolistics techniques. In addition, analysis of several plant promoters located 5' of genes using transgenic plant systems showed that regions in the range of several hundred basepairs to about one kilobase could produce faithful expression patterns of reporter genes in vivo. The availability of seed-specific promoters that drive gene expression over the entire period of oil deposition in oil-bearing crops like rapeseed and soybean have been a major contribution to the success in altering oil composition by genetic engineering. These promoters have ensured that most of the effects on lipid metabolism are confined to storage lipids without significantly affecting lipid metabolism in leaves or other tissues which can otherwise leads to deleterious agronomic effects on the transgenic plants.

Similarly for the oil palm, efforts to modify mesocarp oil composition by genetic engineering would benefit greatly from the availability of temporally-regulated and tissue-targeted gene promoters. Such promoters are preferably able to drive specific expression of introduced genes in the mesocarp during the period of oil synthesis (15-20 weeks after anthesis). In addition, promoters for selective expression of desired genes in other tissues of the oil palm would also be desirable.

SUMMARY OF THE INVENTION

The present invention is based in part on the discovery of regulatory sequences that regulate gene expression in the mesocarp and/or senescent leaves of certain plants. Some aspects of the invention relate to regulatory nucleic acids that modulate expression of a type 3 metallothionein-like gene, MT3-A, in the oil palm. Nucleic acid sequences of the invention may be used to regulate expression of introduced genes in a variety of plant species, and, for example, to target gene expression to the mesocarp or to senescent leaves. The mesocarp often contains the majority of useful compounds, such as oils or carbohydrates, that are found in a fruit, and therefore the ability to target gene expression to the mesocarp is useful, for example, to introduce desirable traits into this tissue. Exemplary desirable traits include the production of oils with modified fatty acid compositions, the production of value added nutritive compounds, the production of pharmaceutically useful polypeptides, etc. Expression of heterologous proteins in senescent leaves is advantageous, in part, because it is unlikely to affect aspects of leaf function, such as photosynthesis, that are important for plant health. Other aspects of the invention relate to metallothionein-like genes and their uses in transgenic plants.

In one aspect, the invention features isolated MT3-A regulatory nucleic acids and complements thereto. In certain embodiments, the MT3-A regulatory nucleic acids comprise nucleic acids that are at least 75% identical to the nucleic acid of SEQ ID No:1. In other embodiments, the MT3-A regulatory nucleic acids comprise nucleic acids that are at least 80%, 85%, 90%, 95%, 98%, 99% or 100% identical to the nucleic acid of SEQ ID No:1. In a further embodiment, the MT3-A regulatory nucleic acids comprise nucleic acids that are a portion of SEQ ID No. 1, such as, for example, 3 consecutive nucleotides, 4 consecutive nucleotides, 5, 10, 15, 20, 25, 30, 35, 40, or 50 or more consecutive nucleotides, or a functionally active assemblage of several portions of the nucleic acid of SEQ ID No: 1. In an another embodiment, the claimed nucleic acid hybridizes with at least a portion of the nucleic acid sequence provided as SEQ. ID. No. 1 or to at least a portion of the complement of the nucleic acid sequence designated as SEQ. ID. No: 1. In preferred embodiments, claimed MT3-A regulatory nucleic acids retain the ability to selectively stimulate gene expression in the mesocarp. In certain embodiments, MT3-A regulatory nucleic acids selectively promote gene expression in the mesocarp, and preferably during the period of oil synthesis. In certain embodiments an MT3-A regulatory nucleic acids selectively promote gene expression in the mesocarp at a time between 12 and 20 weeks and preferably between 15 and 20 weeks after anthesis (w.a.a.). In further embodiments, an MT3-A regulatory nucleic acid selectively promotes gene expression in senescent leaves.

In other aspects, the invention provides probes and primers comprising substantially purified oligonucleotides, which correspond to a region of nucleotide sequence which hybridizes to at least 12 consecutive nucleotides of the sequence set forth as SEQ ID No: 1 or to the complement of the sequence set forth as SEQ ID Nos: 1 or naturally occurring mutants thereof. In certain embodiments, the probe/primer further includes a label group attached thereto, which is capable of being detected.

The invention further provides nucleic acid constructs comprising an MT3-A regulatory nucleic acid operably linked to a recombined nucleic acid. In another aspect the invention describes vectors comprised of an MT3-A regulatory nucleic acid and/or a nucleic acid construct a described above. Such vectors may, for example, be designed for introduction into plant tissues, including plant cells. In a further aspect, the invention relates to host cells transfected with vectors, whether prokaryotic or eukaryotic, and in certain embodiments the host cells are plant cells. In yet another aspect the invention provides transgenic plants and/or transgenic plant tissues; materials or cells that comprise a heterologous form of a functional or non-functional MT3-A promoter and/or a nucleic acid construct or vector of the invention.

The invention further relates to methods of generating transgenic plants and plant tissues. In certain aspects, methods of the invention comprise contacting a plant, plant tissue and/or plant cell with a vector comprising an MT3-A regulatory nucleic acid. Such methods may further involve regenerating one or more whole plants from transformed plant(s), plant tissue or plant cells.

In a further embodiment the invention provides transgenic plants, plant tissues and plant cells comprising an MT3-A regulatory nucleic acid. In certain embodiments, the MT3-A regulatory nucleic acid is inserted in the plant genome at a position different from the position of any endogenous MT3-A regulatory nucleic acids. In many embodiments, the MT3-A regulatory nucleic acid is adjacent to a recombined nucleic acid.

In other aspects the invention provides transgenic palms having a recombined nucleic acid selectively expressed in the mesocarp. In further aspects, the invention provides transgenic palms having a recombined nucleic acid selectively expressed in senescent leaves.

In additional aspects, the invention provides products derived from transgenic plants, plant materials or plant cells of the invention. Such products include a wide range of materials that may generally be produced by biologically catalyzed processes. Such products include for example, but are not limited to, oils, polymers such as polyhydroxybutyrates; vitamins such as carotenoids or tocopherols, celluloses, hemicelluloses etc., polypeptides, particularly polypeptides having pharmaceutical utility and crude preparations containing one or more of the above and a substantial amount of plant material. In certain embodiments, the plant products of the invention are derived, at least in part, from the mesocarp and/or senescent leaves. In further embodiments, the plant products of the invention are not naturally occurring in the host plant but are produced, at least in part, through the action of a gene product whose production is directed, in part or in full, by an MT3-A regulatory nucleic acid. In additional embodiments, the plant products of the invention are naturally occurring in the host plant but in substantially different quantities. In many embodiments, plant products of the invention will contain detectable amounts of nucleic acid comprising an MT3-A regulatory nucleic acid. In another aspect, the invention provides methods for determining whether a plant, plant tissue, plant cell, plant material or plant product comprises a transgenic MT3-A regulatory nucleic acid, comprising detecting the presence of such a nucleic acid in a sample.

In another aspect, the invention features compositions that modulate an MT3-A regulatory nucleic acid, comprising molecules that modulate (agonize or antagonize) transcription from an MT3-A regulatory nucleic acid, thereby activating, increasing or suppressing the expression level of a gene under the control of the MT3-A regulatory nucleic acid. Particularly preferred molecules for use as such modulating compositions are selected from the group consisting of: proteins, peptides, peptidomimetics, metals, other small molecules (e.g. carbohydrates, lipids, plant hormones, or other small organic molecules) or nucleic acids (e.g. sense, antisense, ribozyme and triplex nucleic acid constructs).

In yet another aspect, the invention provides assays for screening test compounds to identify molecules that modulate (agonize or antagonize) transcription from an MT3-A regulatory-nucleic acid, thereby activating, increasing or suppressing the expression level of a gene under the control of the regulatory nucleic acid. In one exemplary embodiment, the assay is essentially comprised of the steps of: (i) combining a test compound with a functional reporter construct comprised of a gene encoding a reporter molecule (e.g., luciferase or GFP) under the control of an MT3-A promoter or regulatory sequence; and (ii) detecting the level of expression of the reporter gene, wherein a statistically significant change in the level of expression (relative to expression in the absence of the test compound) indicates that the test compound modulates (agonizes or antagonizes) transcription from an MT3-A regulatory nucleic acid.

In a further aspect, the invention provides methods of generating transgenic plants comprising a heterologous nucleic acid encoding a metallothionein or a nucleic acid encoding a metallothionein that is expressed from a heterologous promoter. In one embodiment, nucleic acids encoding a metallothionein comprise nucleic acids that are at least 75% identical to one or more of the nucleic acids of SEQ ID Nos:2-4. In other embodiments, nucleic acids encoding a metallothionein comprise nucleic acids that are at least 80%, 85%, 90%, 95%, 98%, 99% or 100% identical to the nucleic acid of SEQ ID Nos:2-4. In a further embodiment, the nucleic acids encoding a metallothionein comprise nucleic acids that are a portion, or a functionally active assemblage of several portions of, the nucleic acid of SEQ ID No:2-4. In preferred embodiments, nucleic acids encoding a metallothionein retain the ability to interact with metals, and particularly transitional metals and/or d10 metals.

Other features and advantages of the invention will be apparent from the following detailed description and claims.

BRIEF DESCRIPTION OF THE FIGURES

FIG. 1a provides the nucleotide and deduced amino acid sequences of pOPSN6 (cDNA sequence of MT3-A). The ORF is capitalised and the UTRs are in lower case. The consensus sequences for translation start and polyadenylation signal are doubly underlined. The amino acids are shown in single letter codes. (SEQ ID NO: 2)

FIG. 1b provides the nucleotide sequence of the cloned 5'-RACE product. The 5' extension to the original cDNA sequence of pOPSN6 and the complementary sequence to the nested primer used in the secondary PCR reaction are bold and underlined.

FIG. 2 provides the comparison of the deduced amino acid sequence of pOPSN6 with several type 1, type 2 and type 3 metallothionein-like genes. Dots have been introduced to optimise alignment. Dark shaded areas represent identical amino acids and light shaded areas represent similar amino acids. Sequences from GenBank and Swiss Prot databases are grouped to reflect the arrangement of Cys-residues.

Type 1 sequences are pea (*Pisum sativum* P20830) (SEQ. ID. NO: 16), maize (*Zen mays* P30571) (SEQ. ID. NO: 17), clover (*Triflium repens* P43399) (SEQ. ID. NO: 18), and rice (*Orzya sativa* Q40633) (SEQ. ID. NO: 19).

Type 2 sequences are rice (*Oryza saliva* D15602), (SEQ. ID. NO: 20), arab (*Arabidopsis thaliana* P25860) (SEQ. ID. NO: 21), kiwi fruit (*Actinidia delicosa* P43390) (SEQ. ID. NO: 22) and castor bean (*Ricinus communis* P30564) (SEQ. ID. NO: 23).

Type 3 sequences are kiwi fruit (*Actinidia delicosa* P43389) (SEQ. ID. NO: 24), banana (*Musa acuminata* 40256) (SEQ. ID. NO: 25) and papaya (*Carica papaya* Q96386) (SEQ. ID. NO: 26).

FIG. 3a shows the alignment between deduced amino acid sequences of pOPSN6 (MT3-A) and pOPSN7 (MT3-B).

FIG. 3b is a table summarising percentages of identity at the nucleotide and amino acid levels between sequences of pOPSN6 and pOPSN7 (cDNA sequence of MT3-B).

Figure 4:
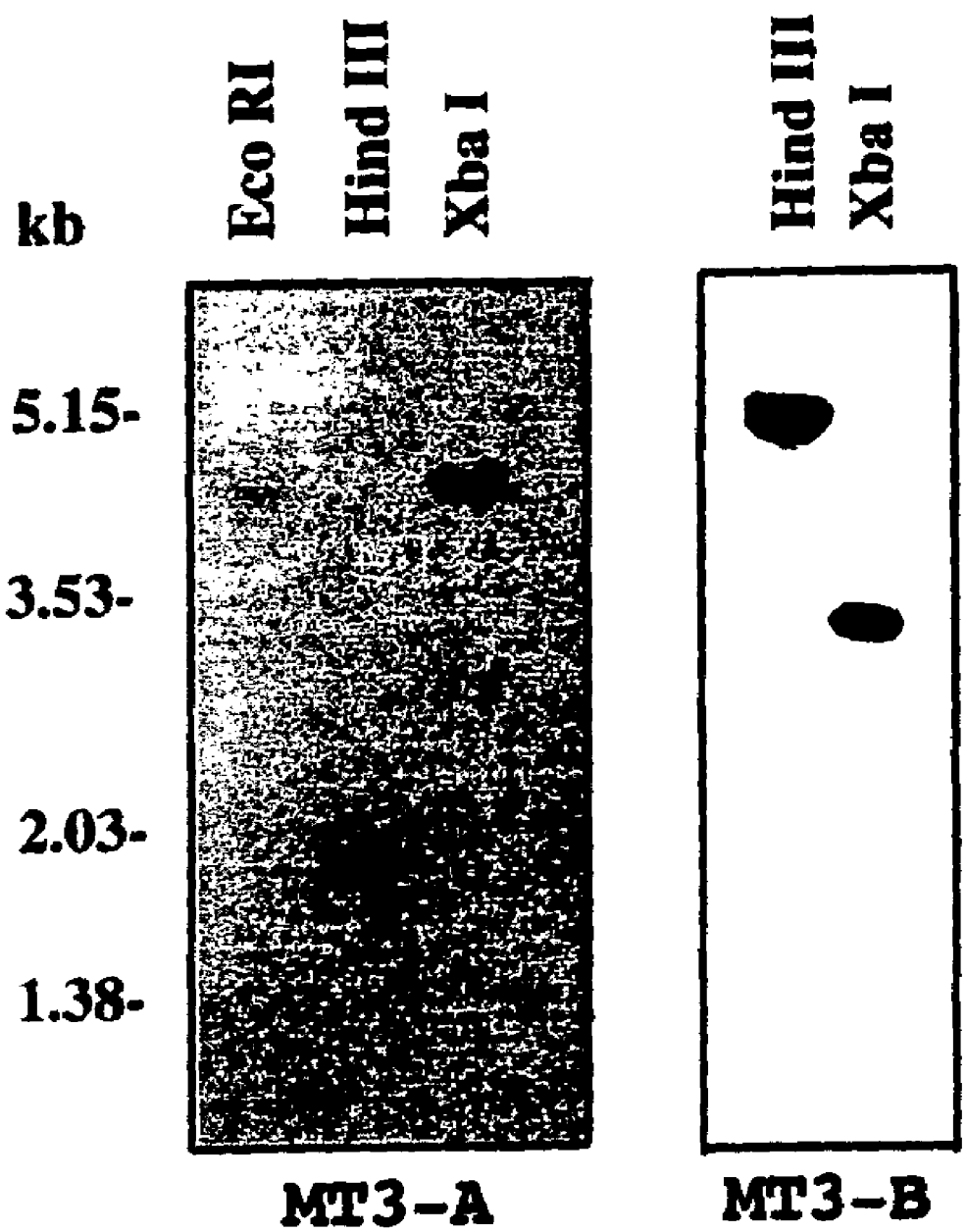

FIG. 4 provides the result of Southern analysis for gene copy number determination of MT3-A and MT3-B. Ten micrograms of oil palm (*Elaeis guineensis*) genomic DNA digested with Eco RI, Hind III or Xba 1, was separated on 0.9% agarose gel, transferred to nylon membrane and probed with gene-specific probes based on 3'UTR of MT3-A and MT3-B gene.

Figure 5:
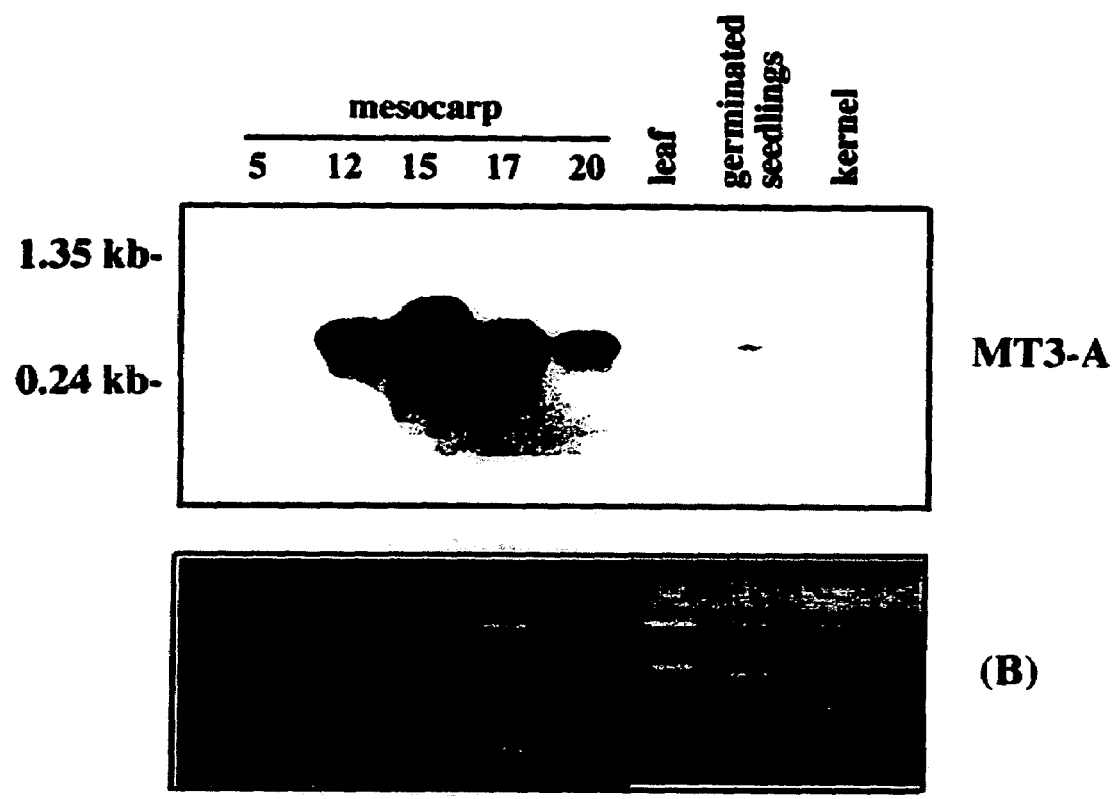

FIG. 5 gives the results of Northern analysis of oil palm MT3-A gene showing its expression pattern in young leaves, germinated seedlings, kernel at 12 w.a.a and mesocarp tissues at different stages (5, 12, 15, 17 and 20 w.a.a) of development. Northern blot containing 2 µg poly (A)⁺ RNA from various oil palm (*E. guineensis*) tissues was hybidised with $^{32}$P-labelled probe prepared using entire insert of MT3-A cDNA. An ethidium bromide stained gel (B) was included to show approximately equal loading of poly (A)⁺ RNA samples.

Figure 6:
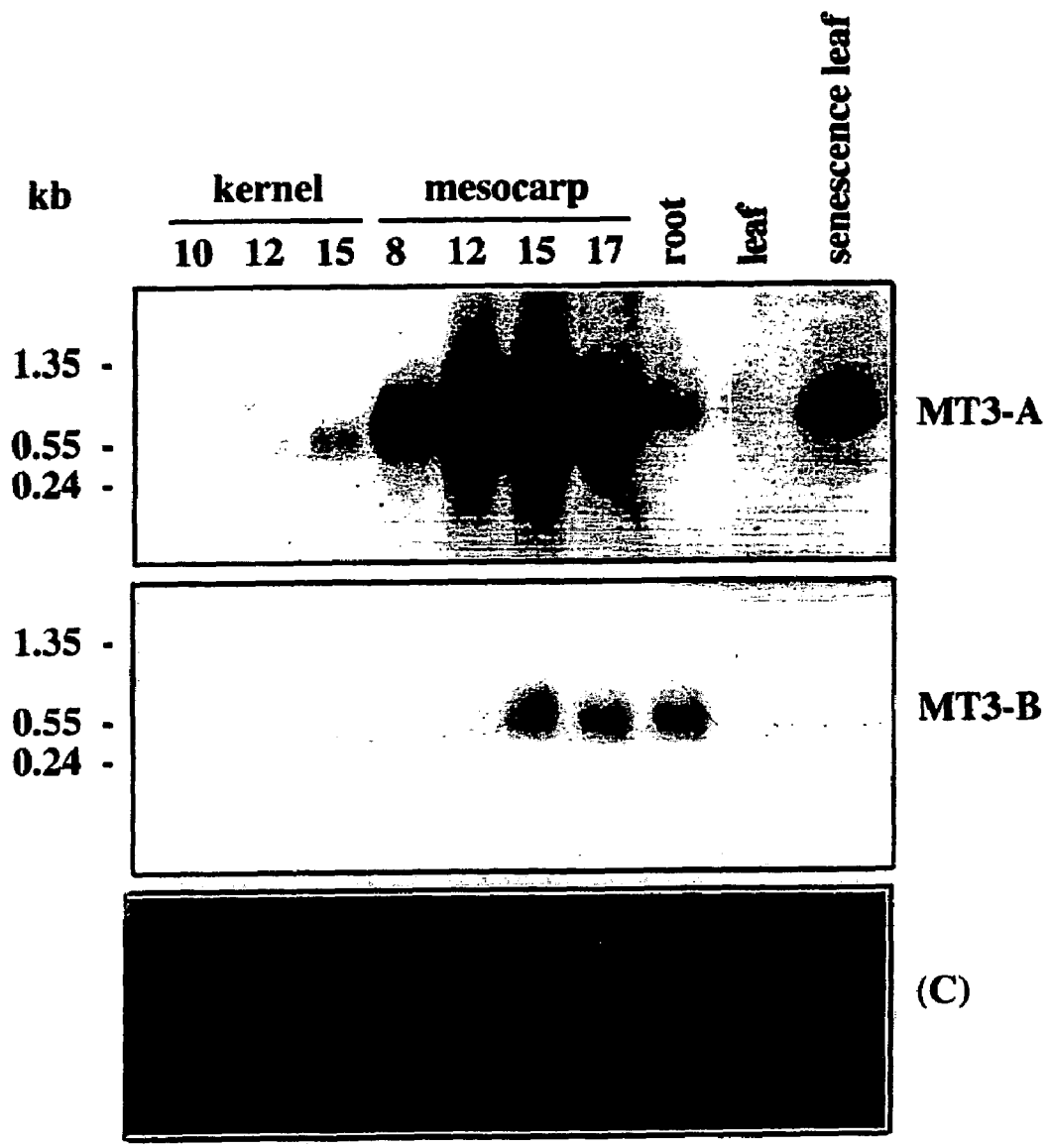

FIG. 6 compares the expression pattern of MT3-A and MT3-B genes in young and senescent leaves, roots, and kernel at 3 different stages (10, 12 and 15 w.a.a) and mesocarp at 4 different stages (8, 12, 15 and 17 w.a.a) of development. Northern blot containing 20 µg total RNA from various oil palm (*E. guineensis*) tissues was hybidised with $^{32}$P-labelled gene-specific probe from 3'-untranslated regions of MT3-A and MT3-B genes (as shown). An ethidium bromide stained gel (C) was included to show approximately equal loading of RNA samples.

Figure 7:
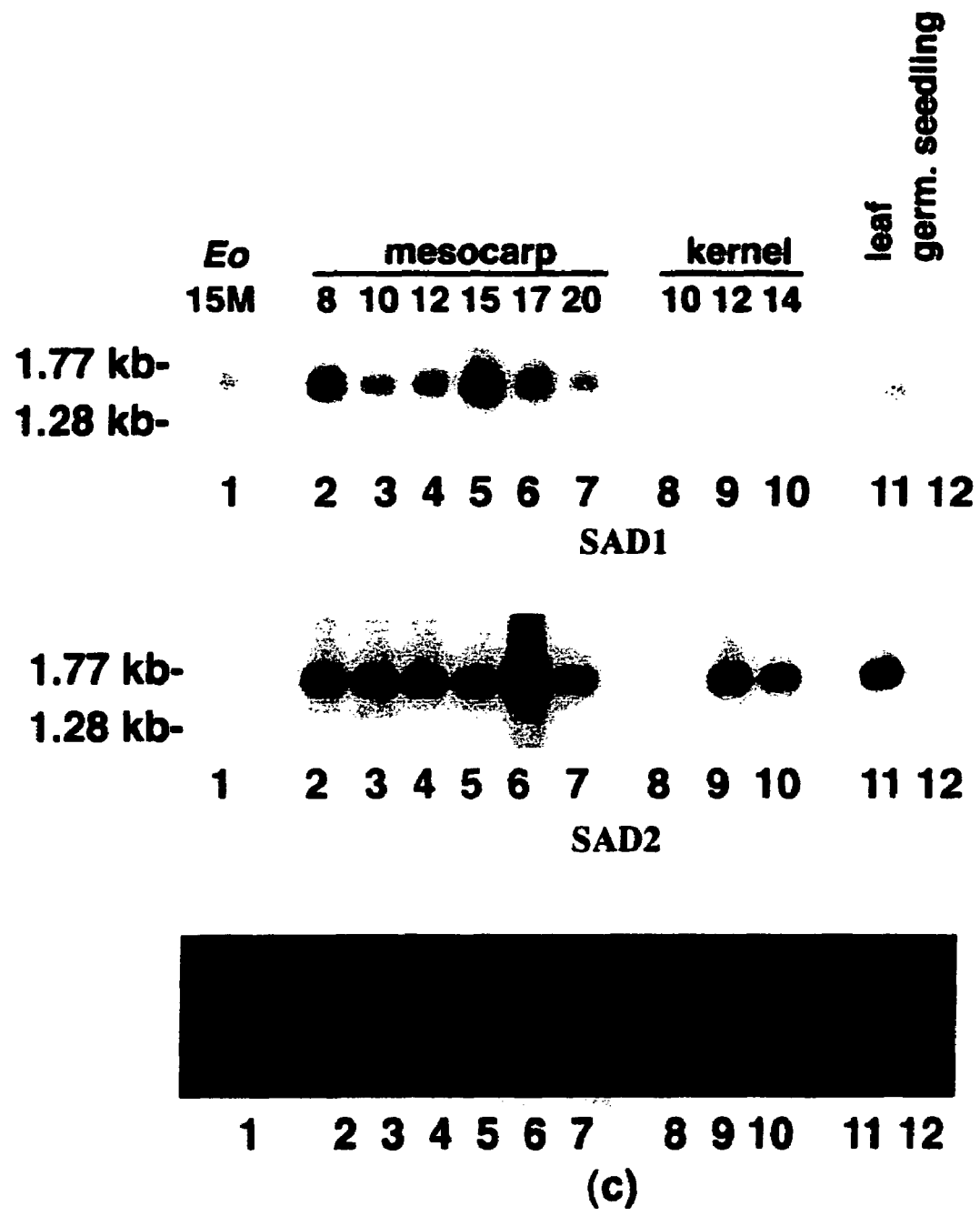

FIG. 7 gives the results of Northern analysis of oil palm stearoyl-ACP desaturase genes showing their expression patterns in young leaves, germinated seedlings, kernel at 3 different stages (10, 12 and 14 w.a.a) and mesocarp at 6 different stages (8, 10, 12, 15, 17 and 20 w.a.a) of development. Northern blots containing 2 µg poly (A)⁺ RNA from various oil palm (*E. guineensis*) tissues (lanes 2-12) were hybidised with $^{32}$P-labelled gene-specific probe from 3'-untranslated regions of oil palm stearoyl-ACP genes, SAD1 and SAD2. Lane 1 represents *E. oleifera* mesocarp at 15 w.a.a. An ethidium bromide stained gel (C) was included to show approximately equal loading of RNA samples.

FIG. 8A shows the products of the primary PCR reaction using primers GSPI and AP 1. Lanes 1, 2, 3 and 4 are the products obtained using 1 µl aliquots of the Dra I, Eco RV, Pvu II and Stu I GenomeWalker libraries, respectively. Lane 5 is the product from control library provided with the GenomeWalker Kit.

FIG. 8B shows the amplified DNA fragment obtained from the secondary PCR reaction using primers GSP2 and AP2. Only the primary PCR product from Dra I library was used in the reaction. The band was subsequently purified from the agarose gel and cloned into the PCR II TOPO vector for sequencing. Lanes 1 and 2 are the secondary PCR products from Dra I library and control library, respectively.

FIG. 9 provides the nucleotide sequence of pMT3A-P1a (the promoter sequence of MT3-A). The putative ethylene responsive element (ERE-reverse), TATA box, the adenine at the 5' end of the 5' RACE product (likely transcription start site) and the ATG codon for start of translation are bold and underlined. (SEQ ID NO: 1).

FIG. 10 shows DNA sequence alignment of pMT3A-Pla (3'-end of nucleotide 1000) (SEQ. ID. NO: 27) and the sequence of the 5' RACE product (nucleotides 1-130 of SEQ. ID. NO: 5) clearly showing 100% homology within the overlapping region (SEQ. ID. NO: 28).

Figure 11A:
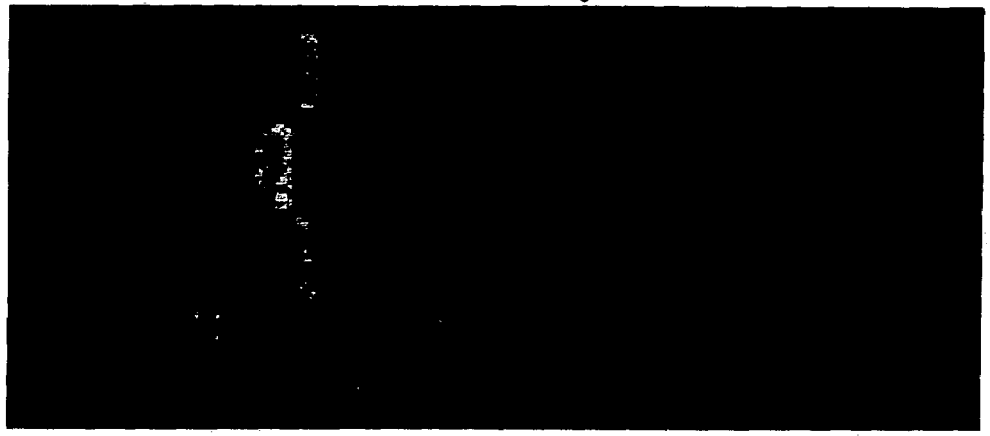
Figure 11B:
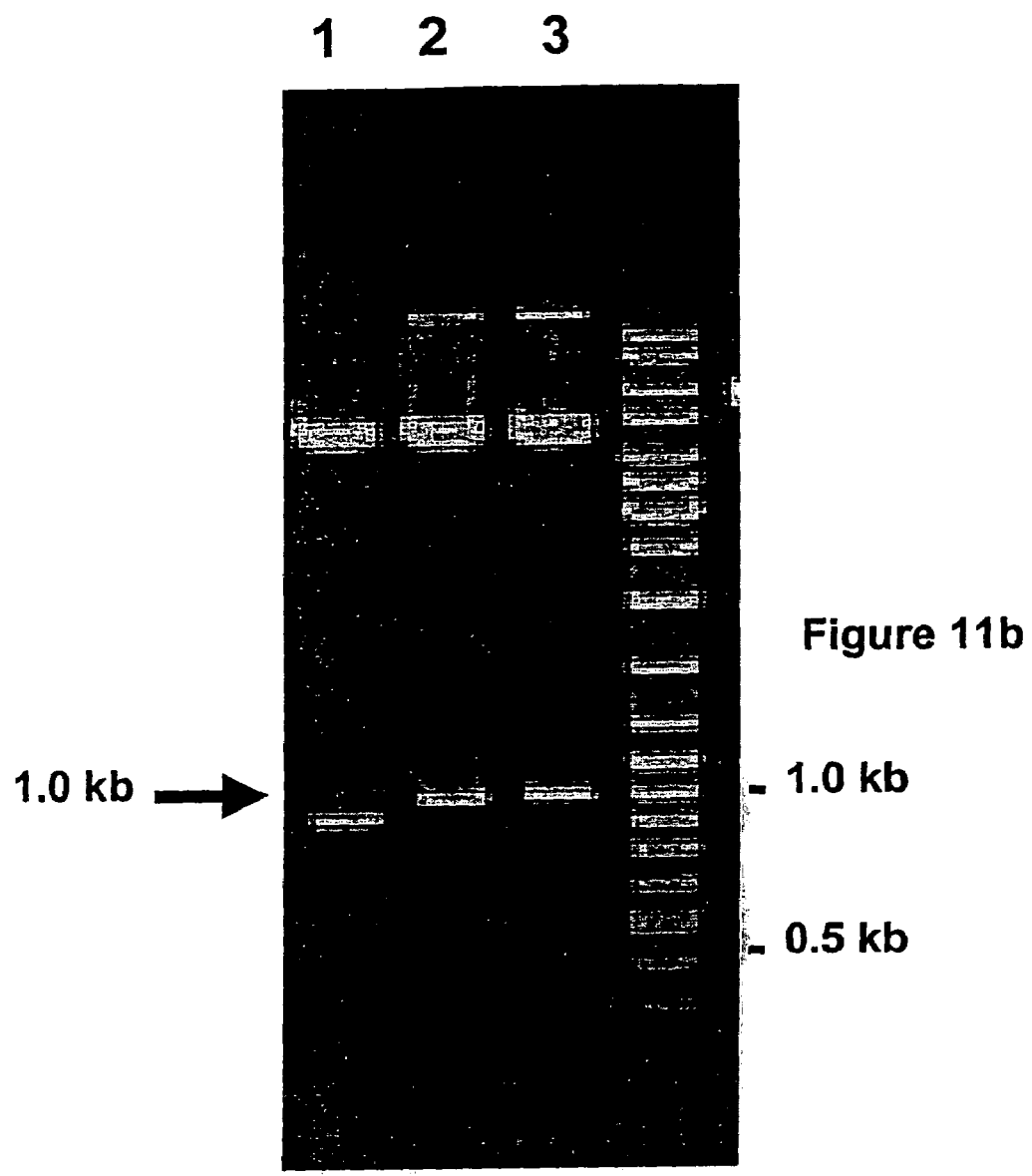

FIG. 11a shows the result of restriction analysis of the chimeric transformation vectors MT3AP-EGFP containing 986 bp MT3-A promoter sequence and GFP as reporter gene. Lane 1: pEGFP vector uncut, Lane 2: MT3AP-EGFP uncut, Lane 3: MT3AP-EGFP digested with Hind III and Pst I FIG. 11b shows the result of restriction analysis of the chimeric transformation vectors MT3AP-GUS containing 986 bp MT3-A promoter sequence and GUS as reporter gene. Digestion was performed with Hind III and Xba I. Lane 1 shows digested products of pBI221. Lanes 2 and 3 show digested products of MT3AP-GUS.

FIG. 12 is a table showing the result of optimising the helium pressure for bombardment for, obtaining GFP expression in mesocarp and control leaf tissue. The optimisation was performed using plasmid HBTIα containing CAMV 35 S enhancer fused to the basal promoter of maize C4PPDK as described by Sheen, J (1993), ["Protenin phosphatase activity is required for light-inducible gene expression in maize". EMBO J 12(9): 3497-3505]. In HBT1α, the α represents SGFP-nos.

FIG. 13 shows expression of GFP in mesocarp tissue slices bombarded with the plasmid MT3AP-EGFP containing the 986 bp MT3-A promoter sequence. No expression was observed when MT3AP-EGFP was used to bombard the control leaf tissues.

FIG. 14 shows the results of histochemical assay to compare expression of GUS between mesocarp and leaf tissues bombarded with the plasmid pBI221 (containing constitutive CaMV 35S promoter) and tissues bombarded with MT3AP-GUS (containing 986 bp oil palm MT3-A promoter sequence). The arrows point to examples of GUS spots on the bombarded tissues.

FIG. 15 shows the coding sequence for MT3-B (SEQ ID NO: 3)

FIG. 16 shows the genomic sequence for MT3-B (SEQ ID NO: 4)

DETAILED DESCRIPTION OF THE PREFERRED EMBODIMENTS

Definitions

The term "fruit" as used herein is intended to encompass any object or objects that are produced by a plant in response to a fertilization event, whether a self- or non-self fertilization, and whether or not the resulting fruit is sterile or non-sterile. For example, both an apple and the seeds of the apple should be viewed as "fruit" herein. As another example, seedless fruits such as grapes and tangerines are fruit. "Fruit" are not limited to edible objects. For example, the poisonous berries of the yew are "fruit" as are any fruits and nuts produced by palms. Other exemplary "fruit" include peanuts, tomatoes, corn, bananas, wheat berries, pears, etc.

"Host cells" or "recombinant host cells" or "recombinant cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

"Homology" or "identity" or "similarity" refers to sequence similarity between two peptides or between two nucleic acid molecules. Homology and identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. A sequence which is "unrelated" or "non-homologous" shares less than 30% identity, though preferably less than 25% identity with a sequence of the present invention. In comparing two sequences, the absence of residues (amino acids or nucleic acids) or presence of extra residues also decreases the identity and homology/similarity.

The term "homology" describes a mathematically based comparison of sequence similarities which is used to identify genes or proteins with similar functions or motifs. The nucleic acid and protein sequences of the present invention may be used as a "query sequence" to perform a search against public databases to, for example, identify other family members, related sequences or homologs. Such searches can be performed using the NBLAST and XBLAST programs (version 2.0) of Altschul, et al. (1990) [J. Mol. Biol. 215:403-10] BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain ammo acid sequences homologous to protein molecules of the invention. To obtain gapped alignments for comparison purposes, Gapped BLAST can be utilized as described in Altschul et al. (1997) Nucleic Acids Res. 25 (17)3389-3402. When utilizing BLAST and Gapped BLAST programs, the default parameters or the respective programs (e.g., XBLAST and BLAST) can be used.

As used herein, "identity" means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well known Smith Waterman algorithm may also be used to determine identity.

The term "isolated" as used herein with respect to nucleic acids, such as DNA or RNA, refers to molecules in a form which does not occur in nature. Moreover, an "isolated nucleic acid" is meant to include nucleic acid fragments which are not naturally occurring as fragments and would not be found in the natural state.

The terms "lipid metabolism" and "fatty acid metabolism" are used interchangeably to refer to the set or a subset of biochemical reactions that are involved in the biosynthesis of fatty acids and/or lipids.

The term "mesocarp" refers to the middle layer of the pericarp. The pericarp is the outer wall of a fruit. The mesocarp is often fleshy or fibrous.

As used herein, the term "nucleic acid" refers to polynucleotides such as deoxyribonucleic acid (DNA), and, where appropriate, ribonucleic acid (RNA). The term should also be understood to include analogs of either RNA or DNA made from nucleotide analogs, and, as applicable to the embodiment being described, single-stranded (such as sense or antisense) and double-stranded polynucleotides. Nucleotide analogs may have modified base moieties, modified sugar moieties, modified phosphate moieties, or a combination thereof. For example a nucleotide analog may be a peptide nucleic acid or a nucleic acid having a transition metal substituted from the phosphate in the backbone.

A "nucleic acid construct" is a nucleic acid comprising a first nucleic acid and a second nucleic acid, wherein the first nucleic acid is adjacent to the second nucleic acid, and wherein the first and second nucleic acids are not adjacent in a naturally occurring genome.

The terms "oil" and "lipid" are used interchangeably herein to refer to any material or mixture of materials that is primarily composed of one or more highly hydrophobic substances such as fatty acids or true fats (e.g. esters of fatty acids and glycerol); lipids (eg. phospholipids, cerebrosides, waxes); and lipoproteins.

The term "operably linked" is used herein to refer to the relationship between a regulatory sequence and a gene. If the regulatory sequence is positioned relative to the gene such that the regulatory sequence is able to exert a measurable effect on the amount of gene product produced, then the regulatory sequence is operably linked to the gene.

A "plant cell" is a cell derived, directly or indirectly, from a plant or a portion of a plant. This term includes plant cell lines that have been propagated through multiple generations. A plant cell is also intended to include cells as present in a plant or plant material.

"Plant material" refers to any material derived from a plant, including for example, but not limited to, fruits, seeds, bark, oils, starches, saps, pollen, petals, sepals, roots, and fragmentary portions thereof. Plant material also includes, for example, plant cells and plant tissue.

"Plant tissue" refers to any portion of a plant that includes a plurality of cells (living or dead) and some extracellular matrix. Plant tissues include, for example, but are not limited to, seeds, fruits, leaves, roots, endosperm, xylem, phloem, etc.

A "recombined nucleic acid" is any nucleic acid that has been placed adjacent to a second nucleic acid by recombinant DNA techniques. A "recombined nucleic acid" also includes any nucleic acid that has been placed next to a second nucleic acid by a laboratory genetic technique such as, for example, transformation and integration, transposon hopping or viral insertion. In general, a recombined nucleic acid is not naturally located adjacent to the second nucleic acid.

A "regulatory element", also termed herein "regulatory sequence" is intended to include elements which are capable of modulating transcription from a core promoter and include elements such as enhancers and silencers. The term "enhancer", also referred to herein as "enhancer element", is intended to include regulatory elements capable of increasing, stimulating, or enhancing transcription from a basic promoter. The term "silencer", also referred to herein as "silencer element" is intended to include regulatory elements capable of decreasing, inhibiting, or repressing transcription from a basic promoter. Regulatory elements can also be present in genes other than in 5' flanking sequences. Thus, it is possible to have regulatory elements located in introns, exons, coding regions, 3' flanking sequences, etc.

A "reporter gene" is any gene encoding a gene product such as a protein (reporter protein) or mRNA (reporter mRNA) which can readily be detected. Reporter proteins may include, but are not limited to fluorescent proteins (eg. Green Fluorescent Protein, Red Fluorescent Protein), chromogenic enzymes (eg. beta-galactosidase, alkaline phosphatase, beta-glucuronidase) and fluorogenic enzymes (eg. luciferase).

The term "selectively" as used herein in reference to gene expression is intended to mean that expression of the gene is higher, and preferably 2, 5, or 10 times higher, in a particular tissue or cell type than the averaged level of expression measured in other tissues or cell types (eg. as compared to expression level measured in a whole plant homogenate). For example, the MT3-A gene is selectively expressed in the mesocarp because expression of this gene, as measured by Northern blot, is substantially higher in the mesocarp than in other tissues measured. The MT3-A gene is also selectively expressed in senescent leaves.

"Small molecule" as used herein, is meant to refer to a compound, which has a molecular weight of less than about 5 kD and most preferably less than about 2.5 kD. Small molecules can be nucleic acids, peptides, polypeptides, peptidomimetics, carbohydrates, lipids or other organic (carbon containing) or inorganic molecules. Most plant hormones, such as giberellins, auxins, abscisic acids, cytokinins etc., are also small molecules.

As used herein, the term "specifically hybridizes" refers to the ability of a nucleic acid probe/primer of the invention to hybridize to at least 12, 15, 20, 25, 30, 35, 40, 45, 50 or 100 consecutive nucleotides of a target gene sequence, or a sequence complementary thereto, or naturally occurring mutants thereof, such that it has less than 15%, preferably less than 10%, and more preferably less than 5% background hybridization to a cellular nucleic acid (e.g., mRNA or genomic DNA) other than the target gene. A variety of hybridization conditions may be used to detect specific hybridization, and the stringency is determined primarily by the wash stage of the hybridization assay. Generally high temperatures and low salt concentrations give high stringency, while low temperatures and high salt concentrations give low stringency. Low stringency hybridization is achieved by washing in, for example, about 2.0×SSC at 50° C., and high stringency is achieved with about 0.2×SSC at 50° C. Further descriptions of stringency are provided below.

As used herein, the term "regulatory nucleic acid" refers to a nucleic acid that activates and/or regulates expression of a selected DNA sequence when such a DNA sequence is operably linked to the regulatory nucleic acid. The term "5' flanking sequence" can include regulatory nucleic acids, but is intended to refer more generally to any nucleic acid sequence located upstream of the transcription initiation site. Thus, a "5' flanking sequence" of an MT3-A gene is intended to include any nucleic acid sequence located upstream of the transcription initiation site and is not required to have any transcriptional activity. The term "core promoter" as used herein is intended to refer to the minimal regulatory nucleic acid that is capable of initiating transcription of a selected DNA sequence to which it is operably linked. The term "core promoter" is intended to represent a promoter element providing basal transcription. A core promoter frequently consists of a TATA box or TATA-like box and complexes with an RNA polymerase. A regulatory may or may not include a core promoter.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". Expression vectors of utility in recombinant DNA techniques are often in the form of "plasmids" which refer to circular double stranded DNA loops which, in their vector form are not bound to the chromosome. Viral vectors are also frequently used as expression vectors.

Regulatory Nucleic Acids

One aspect of the invention pertains to isolated nucleic acids selected from the group consisting of a nucleic acid having SEQ ID No: 1, functional variants and fragments thereof, MT3-A regulatory elements, equivalents to any of these nucleic acids, and complements to any of these nucleic acids. The invention also pertains to nucleic acids capable of hybridizing to the nucleic acid sequence shown SEQ ID No: 1 or a complement thereof. Also within the scope of the invention are nucleic acids which are homologous, e.g., 80%, 85%, 90%, 95%, 98%, 99% or 100% identical to any of the above-recited nucleic acids. Accordingly, the invention provides nucleic acids which are capable of functioning as a promoter, nucleic acids which are capable of functioning as a regulatory element, as well as nucleic acids which do not necessarily function as either. A "functionally active" nucleic acid as used herein with respect to transcriptional regulatory sequences is a nucleic acid that is capable of modulating transcription of a gene to which it is operably linked. Functionally active nucleic acids may be one of the nucleic acids above, including nucleic acid fragments. Thus, a "functionally active" nucleic acid is intended to include nucleic acids capable of functioning as a promoter or as a regulatory element in appropriate conditions. A functionally active fragment of the nucleic acid can be a portion of the nucleic acid which provides mesocarp-selective expression and/or senescent leaf-selective expression. A preferred portion of the nucleic acid provides tissue specific expression substantially similar to the tissue distribution and/or temporal pattern of MT3-A. It is also understood that promoters are often modular in structure, with regulatory elements that greatly affect function and other inter-element sequences with little importance except, in certain instances, to proved the appropriate spacing between regulatory elements. Accordingly, a functionally active nucleic acid may include one or more portions of one of the above nucleic acids assembled, but not necessarily contiguously, to provide a nucleic acid having regulatory activity. The term equivalent of a nucleic acid is understood to include nucleic acids which differ by one or more nucleotide substitutions, additions or deletions from the nucleic acid and which has a similar activity as the nucleic acid.

Preferred nucleic acids of the invention are from the upstream regions of plant genes encoding metallothioneins. A particularly preferred nucleic acid of the invention is an oil palm nucleic acid, such as a nucleic acid having SEQ ID No: 1 or a portion thereof. Regardless of species, particularly preferred nucleic acids are at least 80%, 85% 90%, 95% or 99% similar or identical to the nucleic acids shown in SEQ ID No: 1.

Another aspect of the invention provides a nucleic acid which hybridizes to the nucleic acid shown in SEQ ID No: 1 or complement thereof. Appropriate stringency conditions which promote DNA hybridization, for example, 6× sodium chloride/sodium citrate (SSC) at about 45° C., followed by a wash of 2×SSC at 50° C., are known to those skilled in the art or can be found in Current Protocols in Molecular Biology, John Wiley & Sons, N.Y. (1989), 6.3.1-6.3.6. For example, the salt concentration in the wash step can be selected from a low stringency of about 2×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In a preferred embodiment, a nucleic acid of the present invention will bind to SEQ ID No. 1 under moderately stringent conditions, for example at about 2.0 times SSC and about 40° C. In a particularly preferred embodiment, a nucleic acid of the present invention will bind to SEQ ID No: 1 or complement thereof under high stringency conditions. In certain embodiments the hybridizing nucleic acid is at least 20, 25, 30, 50, 100 or 250 nucleotides in length. Hybridization can be used to isolate nucleic acids of the invention corresponding to MT3-A promoters and regulatory regions from various plant species. A comparison of these nucleic acids should be indicative of regions involved in the regulation of expression of the MT3-A gene, since these regions are expected to be conserved among various species.

Other nucleic acids of the invention are nucleic acids corresponding to one or more discrete regulatory elements, such as enhancers and silencers. Preferred nucleic acids include an ERE box and/or TATA box as identified in FIG. 9.

Any nucleic acid fragment of the invention can be prepared according to methods well known in the art and described, e.g., in Sambrook, J. Fritsch, E. F., and Maniatis, T. (1989 Molecular cloning a laboratory manual (second edition). New York: Cold Spring Harbor Laboratory Press) Molecular Cloning: A Laboratory Manual, Cold Spring Harbor Laboratory Press, Cold Spring Harbor, N.Y.). For example, discrete fragments of the promoter can be prepared and cloned using restriction enzymes. Alternatively, discrete fragments can be prepared using the Polymerase Chain Reaction (PCR) using primers having an appropriate sequence, such as a sequence in SEQ ID NO: 1 or complement thereof.

In yet another embodiment of the invention, the isolated nucleic acid comprises a nucleic acid sequence of SEQ ID No: 1 or portion thereof which has been modified, e.g., by adding, deleting, or substituting one or more nucleic acid residues. Such modifications can modulate the transcriptional activity of the MT3-A regulatory nucleic acid. For example, a modification can increase or decrease the activity of a promoter or regulatory element. A modification can also affect the tissue specificity of a promoter or regulatory element. Thus, for example, an MT3-A regulatory nucleic acid may be modified to stimulate transcription in only one of the tissues in which it is normally expressed, such as the mesocarp or senescing leaves.

Desired modifications of an MT3-A promoter or regulatory element can be generated according to methods that, in view of this specification, are well known in the art, such as by site-directed or random mutagenesis. The activity of the modified promoter or regulatory element can then be tested, e.g., by cloning the modified promoter upstream of a reporter gene, transfecting the construct into plant cells, such as plant mesocarp or leaves or a cell suspension, and measuring of the level of expression of the reporter construct. Such methods are further described in the examples. The activity of the modified promoter or regulatory element can also be analyzed in vivo in transgenic plants. It is also possible to create libraries of modified fragments which can be screened using a functional assay, in which, for example, only modified promoters or regulatory elements having the desired activity are selected. These assays can be based, e.g., on the use of reporter genes providing resistance to specific selection agents such as herbicides or antibiotics, e.g. kanamycin. Selection of cells having a reporter construct containing a promoter or regulatory element having the desired modification can be isolated by culture in the presence of the selection agent.

Also within the scope of the invention are nucleic acid constructs comprising an MT3-A regulatory nucleic acid operably linked to a recombined nucleic acid to be transcribed. The MT3-A regulatory nucleic acid can be, e.g., any of the above-described fragments or variants, and is preferably functional. The MT3-A regulatory nucleic acid can also be a combination of several fragments or regulatory elements having a sequence from SEQ ID No: 1 or modified form thereof, as well as multimers of one or more of these fragments or regulatory elements or modified form thereof. The promoter can also contain regulatory elements derived from other genes.

In many embodiments, the recombined nucleic acid to be transcribed encodes a protein or peptide. The protein can be any protein useful in producing desired qualities or products in the target tissue (eg. mesocarp or senescent leaves). In certain embodiments, the protein is involved in fatty acid and/or lipid metabolism, such as: ACCases (EC 6.4.1.2), such as homomeric acetyl-CoA carboxylase, heteromeric acetyl-CoA carboxylase subunits, acyl carrier proteins, malonyl-CoA:ACP transacylases (EC 2.3.1.39), ketoacyl-ACP synthases (KAS) (EC 2.3.1.41), such as KAS I, KAS II, KAS III, ketoacyl-ACP reductases (EC 1.1.1.100), 3-hydroxyacyl-ACP dehydrases (EC 4.2.1.17), enoyl-ACP reductases (EC 1.3.1.44), stearoyl-ACP desaturases (EC 1.14.99.6), acyl-ACP desaturases other than stearoyl-ACP desaturases, acyl-ACP thioesterase (EC 3.1.2.14), FatA, FatB, glycerol-3-phosphate acyltransferases (EC 2.3.1.15), 1-acyl-sn-glycerol-3-phosphate acyltransferases (EC 2.3.1.51), plastidial cytidine-5'-diphosphate-diacylglycerol synthases (EC 2.7.7.41), plastidial phosphatidylglycerophosphate synthases (EC 2.7.8.5), plastidial phosphatidylglycerol-3-phosphate phosphatases (EC 3.1.3.27), phosphatidylglycerol desaturases (palmitate specific)(EC 1.14.99.-) (FAD4), plastidial oleate desaturases (FAD6) (EC 1.14.99.-), plastidial linoleate desaturases (FAD7/FAD8)(EC 1.14.99.-), plastidial phosphatidic acid phosphatases (EC 3.1.3.4), monogalactosyldiacylglycerol synthases (EC 2.4.1.46), monogalactosyldiacylglycerol desaturases (palmitate-specific), (EC 1.14.99.-) (FAD5), digalactosyldiacylglycerol synthases (EC 2.4.1.184) (DGD1), sulfolipid biosynthesis proteins, long-chain acyl-CoA synthetases (EC 6.2.1.3), ER glycerol-3-phosphate acyltransferases (EC 2.3.1.15), ER 1-acyl-sn-glycerol-3-phosphate acyltransferases (EC 2.3.1.51) (eg. "Cocos nucifera" type and "Brassica napus" type), ER phosphatidic acid phosphatases (EC 3.1.3.4), diacylglycerol cholinephosphotransferasesg (EC 2.7.8.2), ER oleate desaturases (FAD2) (EC 1.14.99.-), ER linoleate desaturases (FAD3) (EC 1.14.99.-), ER cytidine-5'-diphosphate-diacylglycerol synthases (EC 2.7.7.41), ER phosphatidylglycerophosphate synthases (EC 2.7.8.5), ER phosphatidylglycerol-3-phosphate phosphatases (EC 3.1.3.27), phosphatidylinositol synthases (EC 2.7.8.11), diacylglycerol acyltransferases (EC 2.3.1.20), delta-8 sphingolipid desaturases, oleate 12-hydroxylases, bifunctional oleate 12-hydroxylase:desaturases, delta 12 fatty acid acetylenases, delta 12 fatty acid epoxygenases, diacylglycerol kinases (EC 2.7.1.107), cholinephosphate cytidylyltransferases (EC 2.7.7.15), choline kinases (EC 2.7.1.32), phospholipase C (EC 3.1.4.11), phospholipase D (EC 3.1.4.4), phosphatidylserine synthases, phosphatidylserine decarboxylases (EC 4.1.1.65), phosphatidylinositol-3-kinases (EC 2.7.1.137), phosphatidylinositol-4-kinases (EC 2.7.1.67), ketoacyl-CoA synthases (KCS), beta-ketoacyl reductases (involved in wax biosynthesis), wax synthases, oleosins, oleosin-like proteins, 3-ketoacyl-CoA thiolases (EC 2.3.1.16), acyl-CoA oxidases (EC 1.3.3.6) and acyl-CoA dehydrogenases (EC 1.3.99.2).

In general, crude palm oil contains a few minor components of high value including lycopene (a carotenoid), tocopherols and tocotrienols (vitamin E), sterols and squalene. In certain aspects, the recombined nucleic acid to be transcribed encodes a protein involved in the biosynthesis of one or more of these compounds. Exemplary proteins include: Hydroxymethylglutaryl-CoA reductase (NADPH)(EC 1.1.1.34); Mevalonate kinase (EC 2.7.1.36); Phosphomevalonate kinase (EC 2.7.4.2); Diphosphomevalonate decarboxylase (EC 4.1.1.33); Geranyltranstransferase (EC 2.5.1.10); Farnesyltaanstransferase (EC 2.5.1.29); Dimethylallyltranstransferase (EC 2.5.1.1); Isopentenyl-diphosphate delta-isomerase (EC 5.3.3.2); Chrysanthemyl pyrophosphate synthase; s-linalool synthase; Geranylgeranyl-diphosphate geranylgeranyltransferase (EC 2.5.1.32); Phytoene synthase; Phytoene desaturase; Lycopene cyclase; Carotene 7,8-desaturase (EC 1.14.99.30); b-carotene hydroxylase; gamma-tocopherol methyl transferase; p-hydroxyphenylpyruvate dioxygenase; Squalene synthetase (EC 2.5.1.21); Squalene monooxygenase (EC 1.14.99.7); Lanosterol synthase (EC 5.4.99.7); Cycloartenol synthase (EC 5.4.99.8); Lathosterol oxidase (EC 1.3.3.2); Cholestenol delta-isomerase (EC 5.3.3.5); 7-Dehydrocholesterol reductase (EC 1.3.1.21). In certain embodiments, expression of one or more of the above enzymes may enhance production of high value biochemicals.

In other embodiments, the protein to be expressed is useful when ingested by humans; for example, a variety of proteins from pathogens are effective as oral vaccines, such as hepatitis B surface antigen, and such proteins may be expressed in the mesocarp of fruits for ingestion. Proteins that promote synthesis of nutritionally valuable compounds, such as proteins involved in the biosynthesis of vitamins may also be expressed to produce fruits having a higher content of such compounds. Proteins may also increase or decrease or otherwise modify the production of fibrous material and/or extracellular matrices so as to alter mesocarp texture and/or toughness.

In further embodiments proteins involved in the biosynthesis of bioplastics, such, as polyhydroxybutyrates may be operably linked to regulatory sequences of the invention. Exemplary enzymes involved in bioplastic biosynthesis include polyhydroxyalkanoate synthase; polyhydroxybutyrate synthase; beta-ketothiolase; acetoacetyl-CoA reductase; phosphotransacetylase; polyhydroxybutyrate depolymerase; etc. In many embodiments, genes encoding the above proteins are bacterial genes or modified genes derived from bacteria.

In another embodiment, the recombined nucleic acid is transcribed into an RNA having an activity, such as an antisense, an RNAi, or a ribozyme. Expression of such nucleic acids can be used, e.g., to reduce or inhibit translation of a MRNA into a specific protein or to reduce transcription.

In yet another embodiment, the nucleic acid to be regulated by an MT3-A regulatory nucleic acid is a reporter gene. Reporter genes include any gene encoding a protein, the amount of which can be determined. Preferred reporter genes include Green Fluorescent Protein (GFP) and many colored variants (RFP, YFP, CFP, BFP) and other fluorescent proteins, the luciferase gene, the beta-galactosidase gene (LacZ), the chloramphenicol acetyl transferase (CAT) gene, the beta-glucuronidase gene (GUS) or any gene encoding a protein providing resistance to a specific chemical.

Probes, Primers and Detection Methods

Moreover, the MT3-A regulatory nucleic acid sequences provide for the generation of probes and primers which can be used, e.g. to identify plant materials derived from a transgenic plant of the invention. Such methods are highly desirable for monitoring the presence of genetically modified plant materials in foods and other substances. The present invention also provides a probe/primer comprising a substantially purified oligonucleotide, which oligonucleotide comprises a region of nucleotide sequence that hybridizes under stringent conditions to at least approximately 6, 8, 10 or 12, preferably about 25, 30, 40, 50 or 75 consecutive nucleotides of SEQ ID No: 1.

In certain embodiments, the probe further comprises a label attached thereto, which is capable of being detected, e.g. the label group is selected from amongst radioisotopes, fluorescent compounds, enzymes, and enzyme co-factors.

In certain embodiments, probes and primers that hybridize to an MT3-A regulatory nucleic acid may, for example, be used to detect the presence of materials derived from a transgenic plant or plant material that contains an MT3-A regulatory nucleic acid. In certain instances, it will be desirable to perform the detection by PCR, in which case two primers will typically be used. It is preferable to select primers that will distinguish between a transgenic version of an MT3-A regulatory nucleic acid and an endogenous version. Such primers may be selected to distinguish by the size of fragment produced and/or by a failure to efficiently amplify the endogenous form. Primers may also be selected to detect other parts of a transgenic nucleic acid that are external to the MT3-A regulatory region. Probes and primers may be used in other detection schemes, such as Southern and Northern blots. In addition, many methodologies involve a global, non-specific amplification of nucleic acids in a sample, followed by probing with a desired probe, and often the desired probe will be part of an array of probes, such as a micorarray. In view of this specification, other methods for detection of transgenic nucleic acids that include an MT3-A regulatory nucleic acid will be apparent to one of skill in the, and such methods are intended to be encompassed hereby.

Plants and Plant Cells

The invention provides plants, plant cells, plant tissue and plant materials that comprise a nucleic acid of the invention, and preferably a nucleic acid construct having a regulatory nucleic acid operably linked to a recombined nucleic acid.

In certain embodiments, regulatory nucleic acids of the invention are useful for directing mesocarp-selective expression in a wide range of plants (and related cells, tissues etc.). Transgenic plants of the invention include, but are not limited to, the palms (members of the family Palmae) and other plants having fruits with oil-bearing mesocarp tissues, such as olives (members of the family Oleaceae) and avocados. Particularly preferred palms include date palms, coconut palms and oil producing palms, which include but are not limited to palms selected from the following genera: *Acrocomia, Astrocaryum, Elaeis, Jessenia, Oenocarpus, Orbignya*, and *Scheelea*. Preferred transgenic plants are members of the species *Elaeis guineensis* Jacq., *Elaeis oleifera* and hybrids thereof. Additional transgenic plants of the invention are plum, mango, tomato, berries, plum, apricot, kiwifruit, melons, cucumber, aubergine, peach, apricot, grape, peach, pear, apple, quince, papaya, and nectarine.

Methods for generating transgenic plants of the invention are, in view of this specification, well known to those of skill in the art. One exemplary type of method involves the bombardment of plant cells or tissue with tungsten (or other relatively inert, dense metal) pellets that have been mixed with the nucleic acid to be introduced. Transformed cells may be selected, often by the presence of a selectable marker present in the nucleic acid. Selectable markers include antibiotic or herbicide resistance genes or chromogenic markers. A commonly used marker is the kanamycin resistance gene. Transformed cells may be cultured to produce callus and, if desired, to regenerate whole plants.

Another exemplary type of method of plant transformation uses the soil bacterium *Agrobacterium tumefaciens*. The nucleic acid to be introduced into the plant is cloned into a vector containing at least one flanking T DNA sequence. When the Agrobacterium containing this plasmid is contacted with the appropriate plant, the DNA positioned near the T DNA sequence is inserted into the genome of cells of the plant. It is contemplated that a variety of cloning vectors and bacterial host strains can be used. For example, Ti-based vectors like pGV3850 into which recombinant plasmids integrate before transfer to plant cells are known as cis-type vectors. There are also Ti-based vector systems in which the recombinant plasmids do not integrate into the resident Ti plasmid or in which large portions of the naturally occurring Ti plasmid are deleted. These binary-type systems, Hoekema et al., Nature, Vol. 303, 179 (1983), or mini-Ti plasmids, Framond et al., Biotechnology, Vol. 1, 262 (1983), have also been shown to introduce DNA into plant cells. These plasmids contain a border sequence (at least one, preferably two) flanking the gene to be introduced into plants. A marker which is selectable or scorable in plant cells is useful but not essential. Such plasmids are typically capable of autonomous replication in *A. tumefaciens* and need not integrate into a resident Ti plasmid. Virulence functions that are useful in effecting transfer to DNA, such as the chimeric genes of the present invention, to plant cells may be provided in trans. Hoekema et al., Nature, Vol. 303, 179 (1983). See also Fraley, R. T. et al., Biotechnology, Vol. 3, 629 (1985); and Klee et al., Biotechnology, Vol. 3, 637 (1985).

Other exemplary methods for introducing nucleic acids into plants include physical methods such as electroporation, chemical methods such as polyethylene glycol (PEG) fusion, and viral methods such as RNA viral vectors which introduce an RNA copy of a gene.

The following is an exemplary methodology for generating a transgenic oil palm. Transgenic oil palm containing the bar gene which confers resistance to the herbicide Basta™ may be produced using the biolistic techniques. Parveez (2000) ["Production of transgenic oil palm (*Elaeis guineensis* JACQ.) using biolistic techniques". Molecular Biology of Woody Plants. (Eds. S. M. Jain and S. C. Minocha). Kluwer Academic Publishers, Vol. 2, 327-350] described the detailed protocol for the production of Bastam resistant transgenic oil palm, which can be used as reference for generating transgenic oil palm containing any other gene(s) of interest. Embryogenic calli derived from embryos, leaflets and roots are used in bombardment. The physical and biological parameters such as helium pressure, microcarrier type and explant source for biolistic transformation of oil palm are optimized. Basta™ and the antibiotic hygromycin are suitable selective agents for transformed cells as they are effective at a much lower concentration (40 mg/ml) compared to other selective agents. The transgenic embryogenic callus is subsequently transferred onto fresh embryogenesis-inducing medium followed by shoot initiation and finally root initiation media for regeneration of transgenic plant.

Modulation of Regulatory Nucleic Acids

In further aspects, the invention provides methods for modulating the regulatory activity of MT3-A regulatory nucleic acids. Such modulation may be achieved, for example, by administering to a plant or plant material, a compound (or mixture of compounds) with modulatory activity, such as a small molecule (such as a plant hormone), protein, RNA, DNA, metal compound, oxidizing agent or virus. The following section describes various exemplary methods that may be used for identifying such compounds.

In one embodiment, a compound can be identified by performing assays in which an MT3-A regulatory nucleic acid binding partner is incubated with such a nucleic acid and the effect of a test compound on the specific binding of the binding partner to the nucleic acid is determined. The binding partner can be, for example, a nuclear extract prepared from a cell expressing MT3-A, such as mesocarp cells or senescing leaf cells. Alternatively, the binding partner can be an isolated, purified or cloned transcription factor. Modulation of binding to the nucleic acid can be determined, e.g., in an electrophoretic mobility shift assay (EMSA), such as those described above. Thus in this exemplary method, a test compound can be incubated together with a nucleic acid, which is preferably labeled, comprising an MT3-A regulatory nucleic acid and the binding partner. The reaction mixture is then subjected to an electrophoresis and the amount of "retarded" protein-nucleic acid complex is compared to the amount of retarded complex from a binding reaction in which the test compound has not been added. A lower level of complex observed in the reaction that contains the test compound compared to the level of complex observed in the reaction that does not contain the test compound indicates that the test compound inhibits or reduces binding of one or more binding partners to the MT3-A regulatory nucleic acid. This type of assay may be performed as a high-throughput assay.

Several in vivo methods may also be used to identify compounds that modulate an MT3-A regulatory nucleic acid. In one embodiment, the invention provides a method comprising incubating a cell expressing MT3-A with a test compound and measuring the MT3-A mRNA or protein level. mRNA levels can be determined by a variety of method known in the art including Northern blot hybridization, RT-PCR, microarray analysis, etc. Protein levels can be determined by a variety of method known in the art including immunoprecipitations or immunohistochemistry using an antibody that specifically recognizes MT3-A.

In a further exemplary embodiment, a reporter construct can be constructed in which a reporter gene is regulated by an MT3-A regulatory nucleic acid. The reporter gene can be any gene encoding a protein which can readily be detected. According to the method of the invention, cells or plants are transformed with the reporter construct. The material can then be incubated in the presence or absence of a test compound for an appropriate amount of time and the level of expression of the reporter gene can be determined. Compounds which produce a statistically significant change in expression of the reporter gene can be identified.

Plant Products

In certain aspects the invention provides products obtained from transgenic plants. Such products are intended to include any material that can be obtained from a plant, whether refined, purified, crude or simply a part or a whole of the plant itself. Exemplary plant products include fruits, juices, saps, syrups, oils, wood chips, nut meats, nectars, phytochemicals (chemicals extracted from plants), flours, proteins, enzymes etc. Plant products may refer to products that are produced by a plant only because of a genetic manipulation. For example, transgenic plants may be designed to produce unusual, novel or non-endogenous oils, novel or non-endogenous proteins, plastics such as polyhydroxybutyrates, etc.

Often plant products will be sufficiently crude that there will be detectable nucleic acids present. In such case, it is possible to ascertain the plant from which the product was derived by analyzing the nucleic acids. For example, a crude extract from the mesocarp of an oil palm fruit may contain nucleic acids (whether free or within remaining intact cells). In such case it is possible to detect the presence of a nucleic acid of interest, such as an MT3-A regulatory nucleic acid, to obtain information about the source plant.

Oil may be extracted from palm tissues in a variety of methods known to one of skill in the art. In certain embodiments, crude palm oil is extracted from the oil palm mesocarp in palm oil mill using mechanical screw press method. An exemplary protocol, described in more detail by Ma A N (1994) ["Extraction of crude palm oil and palm kernel oil. Selected Readings on Palm Oil and its Uses". (Eds. Technical Committee of 1994 Palm Oil Familiarization Programme). Palm Oil Research Institute of Malaysia, 24-34] can be summarized as follows:

Ripe fresh fruit bunches (FFB) are harvested from oil palm plantation and transported with care to the mill to minimize damage. Damaged fruits will result in poor oil quality due to increase levels of free fatty acids. Prior to oil extraction, the FFB are subjected to systematic pretreatments, which begin with sterilization, followed by stripping and finally digestion. During sterilization, the FFB are placed in sterilizer cages and subjected to steam-heat treatment at saturated pressure of 3 $kg/cm^2$ and a temperature of 140° C. for 75 to 90 minutes. Fruit sterilization is performed for the following reasons:
  i) to prevent increase in free fatty acid due to enzymatic activities;
  ii) to facilitate stripping of fruits from the spikelets;
  iii) prepare the fruit mesocarp for digestion process. Subsequently, the FFB undergo stripping process in a rotary drum stripper where the fruits are separated from the spikelets. The released fruits are then subjected to digestion process where they are mashed under steam-heated conditions. This breaks the oil-bearing cells of the mesocaip.

Unrefined oil is pressed out from the pretreated fruits under high pressure using twin screw presses. The crude oil flows into a tank for further purification. The pressure should be optimized to press out all the oil from the mesocarp without breaking the kernel. The fibre and nut (press cake) are conveyed to a depericaper for separation. In some mills, double pressing is employed to minimize nut breakage. In this system, the fibre, after separation from the nut is sent for second pressing to recover the residual oil.

Metallothionein Nucleic Acids and Proteins

In further aspects, the invention relates to metallothioneins, which term includes metallothionein-like proteins, and the nucleic acids encoding such metallothioneins. Metallothioneins (MTs) are an extensive and diverse family of small cysteine-rich proteins that are found in all organisms. Their name derives from their high sulfur content and ability to bind metals in stable metal-thiolate clusters. In view of their metal-binding capacity, it has been suggested that MTs may play a role in the homeostasis of essential metal ions and the detoxification of heavy metals, such as $Cd^{2+}$ or Hg. However, MTs have now been implicated in a wide range of biological processes relating to normal development and both biotic and abiotic responses. There are also numerous indications that MTs are involved in responses to oxidative stress, possibly by cavenging peroxyl and free hydroxyl radicals. Tissue and developmental-specific expression of MT-like genes were demonstrated in several plant species such as *Arabidopsis* and kiwifruit suggesting possible involvement in developmental processes.

In certain embodiments, the invention provides methods of generating transgenic plants comprising a heterologous nucleic acid encoding a metallothionein or a nucleic acid encoding a metallothionein that is expressed from a heterologous promoter. In one embodiment, nucleic acids encoding a metallothionein comprise nucleic acids that are at least 75% identical to one or more of the nucleic acids of SEQ ID Nos:2-4. SEQ ID Nos: 2 and 3 are cDNA sequences. SEQ ID Nos: 4 is a genomic sequence. In other embodiments, nucleic acids encoding a metallothionein comprise nucleic acids that are at least 80%, 85%, 90%, 95%, 98%, 99% or 100% identical to the nucleic acid of SEQ ID Nos:2-4. In a further embodiment, the nucleic acids encoding a metallothionein comprise nucleic acids that are a portion, or a functionally active assemblage of several portions of the nucleic acid of SEQ ID No:2-4. It is further understood that nucleic acids may be interrupted by artificial introns, and it may be advantageous to position leader sequences and trailer sequences, such as terminators, at the 5' and 3' ends, respectively. In preferred embodiments, nucleic acids encoding a metallothionein retain the ability to interact with metals, and particularly transitional metals and/or d10 metals.

In certain aspects the invention provides nucleic acid constructs comprising a metallothionein nucleic acid as described above operably linked to a promoter. The invention further provides vectors comprising the above nucleic acid constructs, and preferred vectors are suitable for transformation of plants and/or plant cells and/or plant tissues. Metallothioneins may be expressed in plants using the normal promoter associated with the gene, or different, i.e. heterologous, promoters. A constitutive promoter such as the CaMV 35S promoter may be selected, or, for example, the nopaline synthase promoter from Agrobacterium. Promoters having different properties, such as greater tissue specificity may also be selected. In this manner it is possible to direct metallothionein expression to a variety of different, selected tissues. It may be desirable to select a promoter from the same organism as the metallothionein is to be expressed in.

Accordingly, in certain aspects the invention provides transgenic plants, tissues and cells comprising a nucleic acid complex as described above. Such plants will typically have a higher level of the expressed metallothionein protein present in transformed cells than in the untransformed state. Such plants may also have a lower level of uncomplexed metals.

The expression of metallothioneins in a tissue or a whole plant has a host of desirable effects. Metallothioneins may help complex certain metals and thereby increase the resistance of cells expressing the metallothionein to metal toxicities. Metallothioneins are also protective against oxidative damage. Metallothioneins also scavenge free radicals and are thus protective against such compounds.

The invention now being generally described, it will be more readily understood by reference to the following examples, which are included merely for purposes of illustration of certain aspects and embodiments of the present invention, and are not intended to limit the invention.

EXAMPLE

Brief Summary of the Examples

Two differentially expressed type 3 MT-like genes were isolated from the oil palm and designated MT3-A and MT3-B. The presence of two copies of type 3 MT-like genes in the oil palm genome was confirmed by Southern blot analysis. The coding sequence of MT3-A and MT3-B are 78% and 70% identical at the nucleotide and amino acid levels, respectively. The homologies within the 3' and 5'-UTR were only 47% and 41%.

Northern analysis showed that both genes are expressed in the mesocarp throughout the ripening period with maximum expression at 15 weeks after anthesis (w.a.a) but MT3-A transcripts were 50 times more abundant than those of MT3-B. Their expression is highly selective to mesocarp tissues. No detectable expression of MT3-A was found in kernel, roots, germinated seedlings and young leaves. Expression of MT3-B was not detected in kernel, germinated seedlings and leaves. However, MT3-B is also expressed at low levels in roots while the expression of MT3-A is induced in senescing leaves.

The highly mesocarp-selective expression of MT3-A may have implications for plant biotechnology generally, and in particular oil palm biotechnology. For example it was found that the MT3-A expression pattern is very similar to that of stearoyl-ACP desaturase, an enzyme with direct involvement in mesocarp oil synthesis. Since MT3-A is highly expressed in the mesocarp tissue of *Elaeis guineensis*, the high yielding commercial oil-bearing species, nucleic acids that regulate MT3-A expression would be valuable for expressing foreign genes aimed at effecting oil modification in the mesocarp. This is a major goal of efforts to improve oil palm crop. Of course, by using the entire promoter of MT3-A, the transgenes would also be expressed in senescing leaves but this is unlikely to be detrimental to the plant as product of the introduced gene would be rapidly degraded as senescence proceeded.

The genome walking approach was used to clone the promoter of MT3-A. Primers from within the coding region of MT3-A were used to capture the promoter or 5' regulatory sequence. The overlapping region of the cloned PCR product showed total homology with MT3-A cDNA sequence. The promoter sequence of MT3-B had been obtained earlier and submitted to the public data base (accession no. AJ236914). There is no significant homology between the promoter sequence of MT3-A and MT3-B. The specificity of MT3-A promoter was confirmed by analysis using transient assay system. In this analysis, the oil palm MT3-A gene promoter was cloned into a promoterless transformation vector containing green fluorescence protein (GFP) as reporter gene and used in bombarding oil palm mesocarp slices and control leaf tissues. Transient expression of GFP observed as green fluorescence spots were detected in the mesocarp slices and not in the control tissue. This result was confirmed using β-glucuronidase (GUS) as reporter gene in the transient assay analysis. Comparison was made between the activity of a constitutive cauliflower mosaic virus (CaMV) 35S promoter and MT3-A promoter. Transient expression of GUS can be detected on both mesocarp slices and control tissues bombarded with gene construct containing the constitutive promoter. Expression was only observed on mesocarp slices bombarded with gene construct containing MT3-A promoter.

Example 1

Screening cDNA Library with Subtracted cDNA Probes

Methods

Biotin labeled mRNA was produced by mixing 10 µg of 5 w.a.a mesocarp mRNA with 30 µl of photoactivable biotin and irradiating the mixture on ice with 300 W reflector flood lamp; for 20 min. The solution was extracted with 2 volumes of water-saturated butanol and the biotin-labeled mRNA recovered in the aqueous phase was ethanol precipitated.

Single stranded cDNA was synthesized from 15 w.a.a mesocarp in 25 µl volume containing 1.0 µg mRNA, 0.5 µl RNase inhibitor (10 U/:l), 5 µl of 5× reverse transcriptase buffer, 1.25 µl of 80 mM sodium pyrophosphate, 1.0 µl of 100 mM dNTP mix, 25 U reverse transcriptase at 42° C. for 1 h. The solution was phenol extracted, ethanol precipitated and the pellet dissolved in 30 µl $H_2O$.

The biotin-labeled 5 w.a.a. mRNA solution was added to the 15 w.a.a. cDNA solution, ethanol precipitated and dissolved in 10 µl $H_2O$ and 10 µl of 2× hybridisation buffer (Stratagene). The mixture was incubated at 100° C. followed by hybridisation at 68° C. for 48 h. A 30 µl volume of 10 mM HEPES/EDTA buffer pH 7.5 and 10 µl streptavidin (1 mg/ml) were added and the tube was incubated at room temperature for 10 min. Phenol/chloroform extraction was performed. The aqueous phase containing subtracted cDNA was removed and ethanol precipitated. Labelled probes were prepared from the subtracted cDNA using random primed DNA labeling system from Stratagene.

Mesocarp cDNA library used for screening with the subtracted cDNA probes were from 15 w.a.a tissues from *E. guineensis* constructed in Uni-ZAP-XR vector (Stratagene). Ten 110 mm petri dishes were used to plate about 200,000 plaque forming units (pfu) for primary screening. The plaques were generated in *E. coli* host strain XL1-Blue. Preparation of cells for plating were prepared based on Sambrook et al. (1989) and plaque lifts were carried out as described in Siti Nor Akmar et al. (1995) ["Construction of oil palm mesocarp cDNA library and the isolation of mesocarp-specific cDNA clones". Asia Pacific Journal of Molecular Biology and Biotechnology, 3: No. 2: 106-111].

Hybridization of probes to membranes was carried out in hybridization buffer containing 5×SSPE (1×SSPE is 0.18 M NaCl, 10 mM $NaH_2PO_4$, pH 7.5, 1 mM EDTA), 5×Denhardt's solution (1×Denhardt's solution is 0.02% each Ficoll 400, bovine serum albumin, and polyvinylpyrrolidone), 0.5% SDS, 100 mg/ml denatured salmon sperm DNA, and $1×10^6$-$5×10^6$ cpm/ml probes. After hybridization the membranes were washed twice in 0.1×SSPE, 0.1% SDS at 65° C. for 20 min. The membranes were subsequently exposed to X-ray films for 48 hr at −80° C.

Results

Biotinylated mRNA from very young mesocarp tissue at 5 weeks after anthesis (w.a.a) was used in hybridisation with single strand cDNA molecules derived from 15 w.a.a mesocarp tissue to remove common sequences including housekeeping genes and other genes expressed in both tissues. The coupled mRNA-cDNA hybrids were efficiently removed with streptavidin. The remaining unhybridised cDNAs which were enriched with sequences specifically expressed in 15 w.a.a mesocarp tissue were labeled and used as probes in screening a 15 w.a.a oil palm mesocarp cDNA library constructed in Uni-ZAP-XR vector (Stratagene). After the secondary screening, five clones which produced strong hybridization signals with the subtractive probes but no signals with 5 w.a.a cDNA probes used as a negative control were selected.

Figure 2:
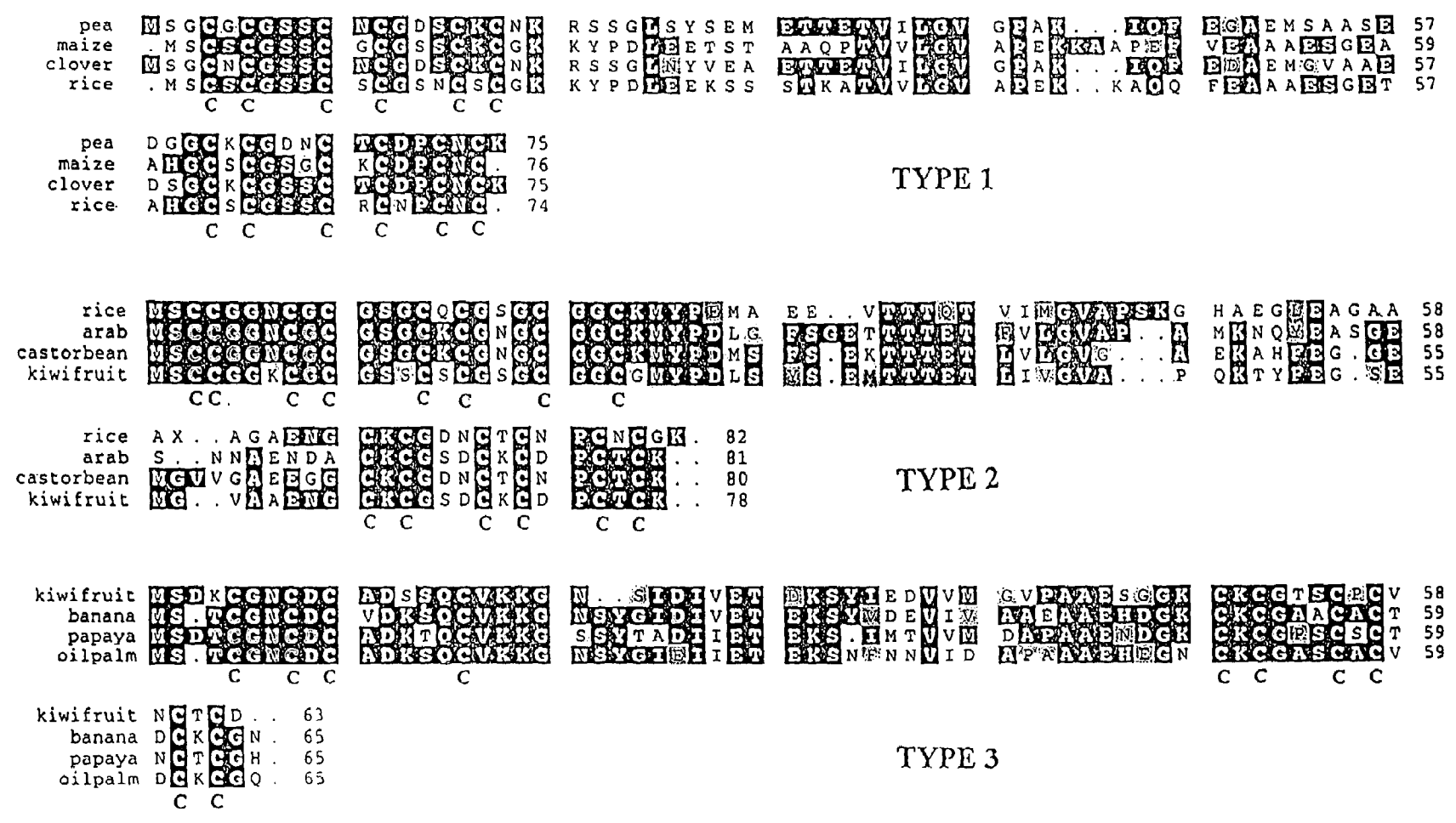

The inserts from all five clones cross-hybridised with each other and were subsequently shown to be identical in sequence. The longest clone was used in rescreening the 15 w.a.a mesocarp cDNA library to obtain a full length clone. About 1% of the recombinant clones from the library produced hybridisation signals indicating that the probe corresponded to a very abundant gene in this tissue. The nucleotide and the deduced amino acid sequence of the biggest clone isolated was designated pOPSN6. pOPSN6 contains a 490 bp insert with an open reading frame (ORF) of 198 bp (FIG. 1). Search for homologies with protein sequences in the databases using BLASTP selected exclusively metallothionein-like (MT-like) proteins and metallothioneins from various organisms as the top 50 best matches. The greatest similarity of 77% identity, was with sequence from *Musa acuminata* (banana; [Q40256]) which belongs to the quite recently identified group of genes isolated from ripening fruit of a few plant species referred to as type 3 MT-like genes. The encoded protein of pOPSN6 appears to have the typical structure of plant MT-like proteins with two cysteine-rich (Cys-rich) terminal domains separated by a cysteine-free (Cys-free) central domain as described by Robinson et al, (1993) ["Plant metallothioneins." Biochem. J. 295:1-10]. Different types (type 1, 2 and 3) of plant MT-like genes are identified by characteristic arrangement of cysteine residues of their encoded polypeptides. FIG. 2 shows the amino acid sequence alignment of the deduced amino acid sequence of the oil palm gene and the sequences of different types of plant MT-like proteins. The oil palm sequence has the same number of cysteine residues which are arranged in a specific and conserved pattern in two domains at the N and C terminals as the other type 3 MT-like genes from different plant species confirming that it belongs to this group of proteins.

Example 2

5'-RACE

Methods

First strand cDNA was synthesized from 15 w.a.a. oil palm mesocarp RNA using antisense 3' sequence specific primer MI (SEQ ID NO: 8) (5' CTA CCA ATA GCA ATC CAT TAA 3') from 3'-UTR of pOPSN6 in a 20 µl reaction mixture containing 5 µg total RNA, 5.0 µl of 2 mM dNTP mix, 2.0 µl of 0.1 M DTT, 1 µl of 200 U/µl Superscript reverse transcriptase (Gibco BRL) and 4 µl of 5× Superscript buffer at 42° C. for 1 hr. The RNA molecules were hydrolysed in 12.5 µl of 0.15 N sodium hydroxide and 1 µl, 0.5 M EDTA, pH 8.0 and incubated at 68° C. for 15 min. A poly(dG) tail sequence was introduced with terminal deoxynucleotidyl transferase in a 20 µl reaction mixture containing 10 mM Tris-acetate pH 7.5, 10 mM magnesium acetate, 50 mM potassium acetate, 0.2 µl 100 mM dGTP and 0.2 µl of 300 U/µl enzyme. Second strand cDNA was synthesized in a 50 µl reaction mixture containing 5.0 µl of 2 mM dNTP, 50 µmol of anchor primer KAI (SEQ ID NO: 29) (5' CU CCC CCC CCC CCC C 3'), 4.5 µl of dG-tailed single-stranded cDNA, 2.6 U of Expand High Fidelity polymerase (Boehringer Mannheim) and 5 µl of 10× enzyme buffer containing 1.5 MM $MgCl_2$. PCR conditions were as follows: 1 cycle: 95° C. for 3 min, 43° C. for 1 min, 72° C. for 2.5 min, followed by 4 cycles; 95° C. for 1 min, 43° C. for 1 min, 72° C. for 2 min.

The PCR product was purified using QIAquick PCR purification kit (Qiagen), and eluted using 50 µlµ$H_2O$. A 5 µl aliquot was added to 50 µl of a secondary PCR mixture containing 5 µl of 2 mM dNTP, 50 pmol of nested primer M32 (SEQ ID NO: 10) (5' CAC CAT GAC AGA AAC ATA TC 3'), 2.6 U of Expand high fidelity polymerase and 1× enzyme buffer containing 1.5 mM MgCl2. The following PCR conditions were used: 1 cycle; 95° C. for 3 min, 51° C. for 1 min. 72° C. for 30 sec, followed by 9 cycles; 95° C. for 1 min, 51° C. for 1 min, 72° C. for 1 min and 30 sec, and 80° C. soak during which 50 pmol of anchor primer KA1 was added followed by 30 cycles; 95° C. for 1 min, 51° C. for 1 min and 72° C. for a min. The PCR product was purified and cloned into PCRII-TOPO vector (Invitrogen).

Results

Total RNA from 15 w.a.a. oil palm mesocarp was used as template in 5' RACE reactions in order to obtain the full length cDNA sequence and to determine the transcription start site of this gene. First strand cDNA synthesis was carried out using primer M1 based on the sequence at the 3' end of the pOPSN6 just prior to the poly(A) tail. Homopolymer tail poly (dG) was subsequently introduced using terminal transferase. Second strand cDNA was synthesized using poly(dC) anchor primer KA1. The anchor primer KA1 together with nested primer based on internal 3' sequence of pOPSN6 were used in the secondary PCR reaction to ensure amplification of the desired sequence. The product from the secondary PCR reaction was cloned and sequenced. The sequence obtained as shown in FIG. 1b showed further 5' extension to the original cDNA sequence of pOPSN6.

Example 3

Screening of Genomic Library

Methods

Ten 110 min petri dishes were used to plate about 200,000 plaque forming units (p.f.u) for primary screening. The plaques were generated in *E. coli* host strain XL1-Blue MRA (P2) Preparation of cells for plating were prepared based on Sambrook et al. (1989) and plaque lifts were carried out as described in Siti Nor Akmar et al. (1995).

Results

About 200,000 clones from an oil palm genomic library constructed in lambda FIX II (Stratagene) were screened using random prime-labeled PCR produced probe containing pOPSN6 sequence. The strongest hybridising phage was isolated and the DNA purified.

Example 4

Southern Blot Analysis and Identification of MT3-B

Methods

Large scale bacteriophage lambda DNA from clones isolated from the genomic library was prepared using the plate lysate method as described in Sambrook et al., (1989). Digestion with restriction enzymes was carried out according to manufacturer's instructions. Electrophoresis of digested samples was performed using 0.9% agarose gel in TAE buffer (40 mM Tris-acetate pH 7.9, 1 mM EDTA). Following electrophoresis, the gel was gently shaken in 0.25 M HCl for 10 min for depurination prior to transfer. The DNA was denatured during overnight transfer onto Hybond N+ (Amersham) membrane under alkaline conditions using 0.4 M NaOH as the transfer buffer. The membrane was rinsed in 2×SSPE before continuing with prehybridization.

PCR produced probes were labeled using Megaprime DNA labeling system from Amersham. Hybridization was performed as described above. For medium stringency washes, the membrane was washed twice in 4×SSPE and 0.1×SDS at 50° C. for 15 mins. The membrane was exposed to Kodak X-OMAT X-ray film for 1 week.

Results

Southern analysis was carried out using various restriction enzymes with pOPSN6 as probe and the appropriate fragment was selected and cloned into pBluescript SK−. This fragment was further digested to produce 6 fragments for subcloning to assist in sequencing.

Example 5

Sequence Analysis

Methods

Plasmid DNA for sequencing was extracted using the Qiagen plasmid mini kit. DNA sequencing was carried out from both directions using ABI automated sequencer. The DNASIS Sequence Analysis Software was used for sequence analysis and search for similarity between nucleotide and amino acid sequences.

Results

Sequence obtained using M13 reverse primer from one end of one of the subclones picked up homology with amino acid sequence at the C-terminal domains of the encoded proteins of plant MT-like genes. Oil palm mesocarp mRNA was used as template in 5' RACE reactions in order to confirm the coding region within the genomic sequence and to determine the transcription start site of this gene. A total of 10 cDNA clones from two independent RACE reactions were sequenced. Eight of these clones had identical sequence and one of them designated pOPSN7, which contained a 399 bp insert provided the longest sequence at the 5' end.

The sequence of pOPSN7 contains a 192 bp ORF coding for 63 amino acids with predicted molecular weight of 6.5 kDa. The sequence contains 76 bp of 5'-UTR. The deduced amino acid sequence of pOPSN7 was found to be different from pOPSN6 but it has the characteristic arrangement of cysteine residues as other plant type 3 MT-like genes. Therefore it was concluded that the genomic clone isolated corresponded to another type 3 MT-like gene from the oil palm which is different from pOPSN6. The two oil palm type 3 MT-like genes were thus designated MT3-A (pOPSN6) and MT3-B (pOPSN7).

Strongly homologous nucleotide sequences between pOPSN6 and pOPSN7 were mainly found in the coding region which has 78% sequence identity (FIG. 3). The homologies within the 3' and 5'-UTR were only 47% and 41%. The identity at the amino acid level was 70% and the homology increased to 86% if conservative substitutions were considered. In addition to the cysteine residues, the first 20 residues from the N-terminal which includes five charged residues (two Ds and three Ks) are highly conserved. The central and C-terminal contain a total of three conserved charged residues (two Es and one K).

A 3.9 kb genomic sequence of MT3-B was obtained and submitted to the EMBL database and was given the accession number AJ236914. The sequence has 2 AT-rich (about 64% AT) introns of 1.432 kb and 306 bp. The introns divide the coding region into 3 exons of 47 bp, 48 bp and 97 bp. The genomic sequence also contains 763 bp of 5' and 1.243 kb of 3' flanking regions.

Genomic Southern analysis was carried out to determine the gene copy number of the oil palm MT3-A and MT3-B (FIG. 4) based on the method described in Example 4. Gene-specific PCR produced probes based on the 3'-UTRs of these genes hybridised to a single fragment in restricted oil palm genomic DNA even with low stringency washing conditions indicating that there is probably only one copy of each gene in the oil palm genome. Oil palm genomic DNA was extracted based on the method of Dellaporta et al. in ["A plant minipreparation: version II. Plant Mol. Biol. Report 1: 19-21]. Southern analysis has also been performed using the entire pOPSN6 insert as probe (data not shown). At low stringency conditions, the probe hybridised to two fragments in restricted oil palm genomic DNA but one of them was much fainter than the other. It was later found that the faint band migrated the same distance as the MT3-B hybridising fragment. This further confirms the presence of two MT3 genes in the oil palm genome which are MT3-A and MT3-B.

Example 6

Northern Blot Analysis

Methods

Different tissues from *E. guineensis*, tenera variety, were used. Fresh fruit bunches were harvested at various weeks after anthesis (w.a.a.) for RNA extraction from the mesocarp and kernel tissues. Young and senescing leaves from 3-4 months polybag seedlings were obtained for RNA preparations. Germinated seedlings after 1 week undergoing germination process were used for RNA extraction.

Total RNA was extracted from various oil palm tissues as describe in Siti Nor Akmar et al. (1994 Detection of differentially expressed genes in the development of oil palm mesocarp. Asia Pacific Journal of Molecular Biology and Biotechnology, 2: No. 2, 113-118). Messenger RNAs from various oil palm tissues were prepared as described in Siti Nor Akmar et al (1994). Two microlitres of mRNA (0.5 µg/µl) was denatured in 18 µl L of solution containing 78% (v/v) deionized formamide, 16% deionized glyoxal, and 10 mM $NaH_2PO_4/Na_2HPO_4$ (pH 7.0) by heating for 15 min at 55° C. followed by immediate cooling. Denatured mRNA was separated on 1.2% agarose gel using 40 mM Tris-acetate (pH 7.0) as electrophoresis buffer. Transfer to nylon membrane (Hybond-N Amersham) was carried out using a vacuum blotter (60 cm $H_2O$, 4 hr) in 20×SSC (1×SSC is 0.15 M NaCl, 15 mM trisodium citrate $2H_2O$, pH7.0). Hybridization and preparation of labeled probes were carried out as described above.

Results

Northern blot analysis was carried out to determine the expression patterns of the oil palm type 3 MT-like genes in various oil palm tissues. Initial analysis was carried out using the entire insert of pOPSN6 (MT3-A cDNA clone) as a probe. Poly $(A)^+$ RNA from mesocarp at different stages of fruit development, from very young (5 w.a.a) to ripe fruits (20 w.a.a) as well as from kernel at 12 w.a.a were used. Poly $(A)^+$ RNA from vegetative tissues (young leaves and germinated seedlings) were also included in the analysis.

It was observed that the MT3-A probe hybridised to a single transcript of about 530 bp (FIG. 5). The expression of MT3-A in the mesocarp tissues was very high and developmentally regulated. MT3-A transcripts were not detectable in the mesocarp at 5 w.a.a. MT3-A gene expression was already high at 12 w.a.a, highest at 15 w.a.a and decreasing significantly as the fruits ripened. The expression was not detectable in kernel at 12 w.a.a and young leaves while a trace level was observed in germinated seedlings. From this analysis the expression of MT3-A appeared to be very strong and specific to the mesocarp.

Northern blot analysis was carried out to compare the expression patterns of the two different type 3 oil palm MT-like genes (MT3-A and MT3-B) using gene-specific probes based on their 3'-UTR. The same probes were used for Southern analysis as described above. Total RNA from different developmental stages of mesocarp and kernel as well as from roots, leaves and senescing leaves were used. Both probes hybridised to similar size transcripts of about 530 bp (FIG. 6). The expression pattern of MT3-A was found to be different from MT3-B. MT3-A expression in the mesocarp can be detected as early as 8 w.a.a., reached a maximum at 15 w.a.a. and decreasing significantly as the fruits ripened. Trace levels of expression was detected in roots and kernel at 15 w.a.a. The expression was not detected in young leaves but was induced in senescing leaves.

The expression of MT3-B in the mesocarp was shown to be 50-fold lower than MT3-A and more specific to the ripening stage. The expression was not detectable in young mesocarp tissue of 8 w.a.a, trace level was observed at 12 w.a.a, highest at 15 w.a.a and reducing slightly at 17 w.a.a. The presence of MT3-B transcripts in 12-weeks mesocarp tissue was confirmed by detection of signals with longer exposure time of the X-ray film. The expression in roots was also high and the level was similar to that observed in 17 w.a.a mesocarp. MT3-B gene transcripts were not detected in kernel, leaves and senescing leaves.

FIG. 7 shows the expression pattern of two different oil palm genes encoding stearoyl-ACP desaturase (SAD), an enzyme directly involved in oil synthesis in the mesocarp tissues. SAD is responsible for converting saturated stearoyl-ACP to monounsaturated oleoyl-ACP. Constitutive expression of SAD2 suggests a possible housekeeping role in membrane lipid biosynthesis. We were more interested in comparing the expression pattern of MT3-A with that of SAD1. SAD1 is believed to have a direct involvement in storage oil synthesis because its expression is induced in lipid-rich mesocarp and kernel tissues in phase with oil synthesis. SAD1 however, may also play a role in membrane lipid synthesis in actively dividing young tissues because it is also quite highly expressed at 8 w.a.a. Similar to SAD1, MT3-A are expressed throughout the ripening period in the mesocarp with an expression peak at 15 w.a.a MT3-A transcripts however, start increasing earlier at around 8 w.a.a and its expression is also induced in senescing leaves.

Example 7

Promoter Isolation

Methods

Isolation of the mesocarp-specific promoter was carried out using the Universal Genome Walker Kit (Clontech). Total DNA was isolated and purified from oil palm spear leaves using DNeasy Plant Mini Kit from Qiagen. Aliquots containing 2.5 µg DNA were digested with restriction enzymes Dra I, Eco RV, Pvu II and Stu I that produce blunt ends and ligated to the GenomeWalker Adaptor creatine the GenomeWalker libraries. Primary PCR was performed using 1 µl aliquots of each library with antisense gene-specific primer GSP1 (SEQ ID NO: 11) 5' CCACACAAGCACAGCTAGCACCA-CACTTG 3' from 3'-terminal of the coding region of pOPSN6 and primer API provided with the Kit. The PCR product was diluted 50× and 1 µl was used in secondary PCR reaction using antisense nested gene-specific primer GSP2 (SEQ ID NO: 12) 5' CTGGCTCTTGTCAGCACAATCG-CAGTTGC 3' from the 5'-terminal of pOPSN6 coding region and primer AP2 front the Kit. PCR was carried out using Advantage Tth Polymerase Mix front Clontech and Perkin-Elmer 9600 thermal cycler following cycle conditions recommended in the GenomeWalker Kit Manual. The secondary PCR product was analysed and purified from agarose gel using gel extraction kit front Qiagen and cloned into PCRII-TOPO vector (Invitrogen). The recombinant clone was sequenced using M 13 forward and reverse primers.

Results

The Universal GenomeWalker kit from Clontech was used to clone the promoter or the 5' upstream regulatory region of MT3-A. Separate aliquots containing 2.5 □g DNA were digested with four different restriction enzymes namely Dra 1, Eco RV, Pvu II and Stu I which produced blunt ends. The GenomeWalker Adaptor was subsequently ligated to the restriction fragments creating four different GenomeWalker libraries. Aliquots from these libraries were amplified using a 29-mer gene-specific primer (GSP1) and primer AP1 from the Adaptor sequence. GSP1 was designed based on the sequence near the 3'-end of MT3-A coding region (bases number 246 until 275 in FIG. 1). GSP1 sequence falls within a fairly variable region of plant type 3 MT-like gene sequences. In this region, 3 out of 8 amino acid residues of MT3-A are different from MT3-B. The size of bands from this primary PCR reaction is shown in FIG. 8A. The Dra L Eco RV and Stu I libraries produced PCR products of about 1.2 kb, 1.0 kb and 0.45 kb, respectively. Since the product of the Dra I library was the biggest, it was selected for further PCR reaction. One microliter of 1/50 dilution of the primary PCR product was used in a second round PCR reaction. In this reaction a 29-mer nested gene-specific primer (GSP2) and nested primer from the Adaptor sequence (AP2) were used. GSP2 was designed based on the sequence at the 5'-end of MT3-A coding region (bases number 111 until 139 in FIG. 1). This secondary PCR reaction specifically amplified fragments containing MT3-A sequence. Fragments produced in the primary PCR reaction due to non-specific binding of primers were not amplified. FIG. 8B showed the product of the secondary PCR reaction. The size of band obtained was approximately 1.2 kb but slightly smaller than the primary PCR product. This is the expected size using the pair of nested primers because the sequence of GSP2 is only 70 bp internal to GSP1. This may also suggest the absence of introns in the genomic sequence. If an intron is present we will expect the secondary PCR product to be smaller. The band was purified from the agarose gel and cloned into PCR II TOPO vector (Invitrogen). Two of the recombinant clones designated pMT3A-P1a and pMT3A-P1b were sequenced from both directions using M13 forward and reverse primer. The sequences of both clones were found to be identical.

The complete sequence of pMT3A-P1a is given in FIG. 9. The sequence has no significant homology with the promoter sequence of MT3-B. A putative TATA box and an ethylene responsive element in reverse orientation (ERE-reverse) were identified at position 953 and 669. The ERE is similar to the ERE AATTCAAA of ripening-specific E4 gene of tomato of Montgomery et al. (1993) ["Identification of an ethylene-responsive region in the promoter of a fruit ripening gene". Proc. Natl. Acad. Sci. USA 90: 5939-5943] and the ERE ATTTCAAA associated with the regulation of carnation glutathione-S-transferase gene (GS7) in senescing tissues. The region containing the ERE in the GST1 gene was shown to operate in orientation—independent manner as described in Itzhaki et al., (1994) "An ethylene-responsive enhancer element is involved in the senescence-related expression of the carnation glutathione-S-transferase (GSTI) gene". Proc. Natl. Acad. Sci. USA 91: 8925-8929].

The sequence of pMT3-AP1a was aligned with the cDNA sequence of the 5' RACE product (FIG. 10). It was found that 113 bp of the 3' terminal region of pMT3A-P1a overlaps with the 5'-terminal sequence of the 5' RACE product. This contains 42 bp of coding sequence. Within the overlapping region, the two sequences are identical. The putative transcription start site is an denine that is 26 bp downstream of the TATA box (FIG. 9), which is consistent with the expected distance of 32±7 (Joshi, C P 1987 An inspection of the domain between putative TATA box and translation start site in 79 plant genes. Nucl. Acids Res. 15, No. 16: 6643-6653). In most genes the transcription start begins with an adenine.

Example 8

Cloning of the MT3-A Promoter into pEGFP-1 and pBI221

Methods

Two primers were used for cloning a 1040 by genomic fragment containing 986 by MT3-A 10 promoter sequence and a further 54 bp sequences downstream into the multiple cloning site of pEGFP-1 (Clontech), a promoterless vector with GFP as reporter gene to produce MT3AP-EGFP. The first primer gC3 (SEQ ID NO: 13) 5' CCC AAG CTT AAA TTA CTG CCA TG 3' is a sense primer front 5' end of the promoter with an Hind III site introduced. The second primer gC4 (SEQ ID NO: 14) 5' AAA ACT GCA GCA GGA AAC CAG AGA C 3' is an antisense primer 16 bases upstream of the translation start site with a Pst I site introduced.

pBI221 plasmid (Clontech) contains β-glucuronidase (GUS) coding region under the control of a strong 35S promoter from cauliflower mosaic virus (CaMV). Plasmid MT3AP-GUS was produced by replacing CaMV 35S promoter in pB1221 with the oil palm MT3-A promoter. The CaMV 35S promoter was removed by digesting pB1221 with Hind III and Xba I. MT3-A promoter was amplified using primers gC3 and gC5. Primer gC5 (SEQ ID NO: 15) 5' TGC TCT AGA CAG GAA ACC AGA GAC 3' is similar to gC4 but in gC5, the Pst I site is replaced with an Xba I site.

The PCR reaction mixture (50 μl) for amplifying MT3-A promoter contained 5.0 μl of 2 mM DNTP, 3.3 μl of 15 μM gC3 primer, 3.3 μl of 15 μM gC4 or gC5 primer, 25 ng of plasmid pMT3A-P1a, 5.0 μl of 10× enzyme buffer containing 1.5 mM $MgCl_2$ and 2.6 U Expand High Fidelity Polymerase (Roche). PCR conditions were as follows: 1 cycle; 94° C. for 3 min, 20 cycles; 94° C. for 1 min, 42° C. for 1 min and 72° C. for 90 sec followed by 1 cycle; 72° C. for 10 min. The PCR product was purified using QIAquick PCR purification kit (Qiagen). Ligation was performed using 1:3 molar ratio of vector:insert in 15.0 μl reaction volume containing 1.5 μl 10× ligase buffer and 1.5 μl of T4 DNA ligase (1 U/μl) and incubation at 16° C. O/N. Two microlitres were used to transform competent cells JM101 as described in Siti Nor Akmar (1999 Structure and regulation of stearoyl-ACP desaturase and metallothionein-like genes in developing fruits of the oil palm (*Elaeis guineensis*) PhD thesis, University of East Anglia, UK). The cells were spread on LB plate containing 40 μl of 20 mg/ml 5-bromo-4-chloro-3-indolyl-μ-D-galactopyranoside (X-gal and 40 μl of 20 mg/ml isopropyl μ-D-thiogalactopyranoside (IPTG)) for blue/white selection of recombinant clones. Plasmid DNA was prepared from selected white colonies using QIAprep spin miniprep kit (Qiagen). Restriction analysis was carried out by digesting with Hind III and Pst I for MT3AP-EGFP or Hind III and Xba I for MT3AP-GUS to confirm the size of insert. Sequencing of MT3AP-EGFP was carried out using EGFP-N sequencing primer from Clontech. The successful replacement of 35S CaMV promoter by the oil palm MT3-A promoter in pBI221 was verified by sequencing with M13 reverse primer.

Results

The 1040 genomic fragment containing 986 bp of mesocarp-specific promoter sequence was cloned into a promoterless transformation vector pEGFP (Clontech) containing GFP as reporter gene and the chimeric transformation vector produced was designated MT3AP-EGFP. Restriction analysis of the MT3AP-EGFP showed the successful cloning of the 1040 bp genomic fragment in pEGFP (FIG. 11a). The approximately 850 bp CaMV 35S promoter was removed from pBI221 by digesting with Hind III and Xba I. The oil palm MT3-A promoter was flanked with Hind III and Xba I sites and ligated to the digested vector and cloned into *E. coli* host. Restriction analysis of the cloned product MT3AP-GUS with Hind III and Xba I showed the successful cloning of the 1040 bp genomic fragment (FIG. 11b). The successful replacement of 35S CaMV promoter by the oil palm MT3-A promoter in pBI221 was verified by sequencing with M13 reverse primer.

Example 9

Biolistic Method and Transient Expression for Promoter Analysis

Methods

Preparation of Tissue Slices

Oil palm fruits (12 w.a.a) were sterilized by soaking in between 20 for 10 minutes followed by 25% chlorox for 20 minutes. The fruits were then rinsed several times with sterile distilled water.

The sterilised fruits were cut into small pieces (1 cm×1 cm). The explants were put on culture media. These cultures were kept at 28° C. in the dark for 24-48 hours before bombardment.

The culture media were based on Murashige and Skoog (MS) salts. MS salts and vitamins were commercially available in dried powder, from DUCHEFA, Biochemicals Plant Cell and Tissue Culture, Haarlem, Netherlands. Every litre of media was prepared by dissolving 4.7 g MS salts and 30 g sucrose in distilled water. Media were solidified with 0.8% (w/v) agar. Media were adjusted to pH 5.8 with 1M NaOH solutions.

Bombardment Procedure

The oil palm fruits and leaf tissues were bombarded with Biolistic Gun He/100 (Biorad) U.S.A The chamber (PDS-1000/He) was sterilised with 100% ethanol.

Microcarrier and macrocarrier were sterilised with 100% ethanol a. Deagglomeration 60 mg of dry gold [microcarrier (1.0 μm in size)] were placed in 1 ml of 100% ethanol in microcentrifuge tube followed by vortexing for 1-2 minutes at 12,000 rpm. This procedure was repeated 3 times. The mixture was sonicated and the supernatant was removed before adding 1 ml of sterile distilled water. The mixture was re-suspended, centrifuged and finally the supernatant was removed.

b. Precipitation of DNA

Two of the plasmids used, HBT1α and MT3AP-EGFP contain green fluorescence protein (GFP) as the reporter gene. HBT1α contains 35S enhancer fused to the basal promoter of maize C4PPDK gene (Chiu et al., 1996 Engineered GFP as a vital reporter in plants. *Current Biology*, 6: No. 3: 325-330). MT3AP-EGFP contains oil palm MT3-A promoter. Promoter analysis was also carried out using β-glucuronidase (GUS) as the repoter gene using constructed plasmid MT3AP-GUS. In MT3AP-GUS, the CaMV 35S promoter in pBI221 was replaced with the oil palm MT3-A promoter. All the plasmids were isolated using QIAgen Spin Miniprep Kit. 30 μg DNA were added to 100 μl aliquot of gold. 100 μl 2.5M CaCl$_2$, 40 μl 0.1M spermidine were added while vortexing. The mixture was centrifuged down at 10,000 rpm. The supernatant, was removed and the microcarrier was washed with 100% ethanol. These steps were repeated twice and finally, the microcarrier was resuspended in 60 μl ethanol and kept at −20° C. until used.

c. Operation 5-10 μl of DNA-coated microcarrier were placed onto the centre of the macrocarrier. The mesocarp tissues were bombarded with 1550 Psi helium pressure and 9 cm distance between macrocarrier and target tissue, with 8 μl gold-coated DNA loaded per bombardment. The leaves (control tissues) were bombarded at 1100 Psi helium pressure and 6 cm distance between macrocarrier and target tissue. The distance between rupture disk to macrocarrier was fixed at 6 mm while the distance between macrocarrier to the stopping plate was fixed at 11 mm. The vacuum pressure was maintained at 27" Hg.

GFP Expression.

The GFP expression was determined using Leica fluorescence microscope fitted with GFP filter set by counting the green fluorescence spots produced.

Results

Transient assay system was developed using biolistic method and mesocarp tissue slices for analyzing the strength and confirming the specificity of oil palm mesocarp-specific promoter. In this method regions of the promoter are ligated upstream to sequence encoding reporter genes such as β-glucuronidase (GUS) and the green fluorescence protein (GFP). Tissue slices bombarded with the promoter:reporter gene construct will be assayed for transient expression of the reporter gene. FIG. 12 gives the results of an optimization experiment to determine the helium pressure and the distance between the macrocarrier and taget tissues suitable for bombarding the mesocarp slices and leaf tissues used as negative control. The optimization experiment was carried out using the plasmid HBTla containing CAMV 35S enhancer and basal promoter of the maize C4PPDK gene (Chiu et al., 1996). In HBT1α, the a represents SGFP-nos.

Mesocarp tissue slices and leaf tissues were bombarded with MT3AP-EGFP using the optimized bombardment parameters. Green fluorescence indicating expression of GFP was observed on bombarded mesocarp slices but not on bombarded leaf tissues (FIG. 13). This confirms that MT3-A promoter is functional and that it has mesocarp-specific activity.

Histochemical Assay for GUS

The substrate used for histochemical localization of β-glucuronidase activity was 5-bromo-4-chloro-3-indolyl glucuronide (X-glue). This substrate works very well, giving a blue precipitate at the site of enzyme activity. The bombarded oil palm tissues were fixed for 5 minutes on ice in fixation solution containing 5% formaldehyde in sodium phosphate buffer pH 7.0. The histochemical assay was performed based on the method of Jefferson et al. (1987) GUS fusions: glucuronidase as a sensitive and versatile gene fusion marker in higher plants, EMBO J 6(13): 3091-3097. The fixed tissues was transferred to X-GLUC solution and incubated at 37° C. for several hours before analysis using a light microscope.

X-GLUC solution
0.2M Na$_2$HPO$_4$
0.2M Na$_2$H$_2$PO$_4$
10% Triton X-100
X-gluc 50 mg/ml
0.25M Na$_2$EDTA
0.005M K Fe$^{2+}$
0.005M KFe$^{3+}$ Results pBI221 is designed to express β-glucuronidase (GUS) fom the strong constitutive CaMV 35S promoter. In order to compare the expression of GUS under the control of the CaMV 35S promoter and the oil palm MT3-A promoter, MT3AP-GUS was produced by replacing the CaMV 35S promoter in pBI221 with MT3-A promoter. pBI221 and MT3AP-GUS were used for bombarding oil palm mesocarp slices at 12 w.a.a. and leaf tissues. Histochemical assay of GUS activity was performed on the bombarded tissues. GUS expression was observed on both mesocarp slices and leaf tissues bombarded with pBI221 (FIG. 14). Expression of GUS was only detected on mesocarp slices bombarded with MT3AP-GUS and no expression was observed on leaf tissues bombarded with this construct. These data further support the results obtained with GFP as the reporter gene (FIG. 13), as it clearly indicates that MT3-A promoter is a functional promoter with mesocarp-specific activity.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. An isolated nucleic acid comprising a regulatory nucleic acid comprising the nucleic acid set forth in SEQ ID No: 1, or fragments of SEQ ID No: 1 with tissue specific promoter activity effective to regulate expression of an operably linked gene in the mesocarp.

2. A transgenic oil palm comprising a recombined nucleic acid that is selectively expressed in the mesocarp, wherein expression of the recombined nucleic acid is regulated by an MT3-A regulatory nucleic acid, and
wherein the MT3-A regulatory nucleic acid comprises SEQ ID NO:1.

3. The transgenic oil palm of claim 2, wherein the recombined nucleic acid is also selectively expressed in one or more senescent leaves.

4. The transgenic oil palm of claim 2, wherein the recombined nucleic acid is selectively expressed in the mesocarp during the period of oil synthesis.

5. The transgenic oil palm of claim 2, wherein the recombined gene encodes a protein selected from the group consisting of: a phospholipase, a desaturase, a thioesterase, a thiolase, a hydroxylase, an oxidase, an acyl transferase, a synthase, a fluorescent protein, a reporter protein and a transcriptional regulator.

6. The transgenic oil palm of claim 2, wherein the recombined gene encodes a protein that is involved in the metabolism of a compound selected from the group consisting of: a lipid, a sterol, a tocopherol, a carotenoid, a bioplastic, a tocotrienol and squalene.

7. A method of obtaining an oil product comprising: (a) providing oil-bearing fruit from the transgenic oil palm of claim 2; (b) extracting oil from the mesocarp of the fruit.

8. A method of claim 7 wherein the oil-bearing fruit is selected from the group consisting of: an oil palm fruit, an olive and an avocado.

9. A method of claim 7 further comprising the step of enriching for one or more desired lipid.

* * * * *

SEQUENCE LISTING

<160> NUMBER OF SEQ ID NOS: 28

<210> SEQ ID NO 1
<211> LENGTH: 1140
<212> TYPE: DNA
<213> ORGANISM: Elaeis sp.

<400> SEQUENCE: 1

```
gcccttacta tagggcacgc gtggtcgacg gcccgggctg gtaaaattac tgccatggag      60
ggtcacaatg atgcaactaa acatgataat ctcatcacct ccatctacat catctttaat     120
cctacatgaa tcattccata tcaaatacct cccaactaaa atcgaacccc atcttcttgt     180
ccaagtgaca aagaatgata ccatggaggc aagcatttaa ccagaactag aagtctgcca     240
aggagtagtt gacagaatcg aaccccatct tattgtccac cattcttgac acaaaaataa     300
cccgtgcaga tagactatag tcaatcgtta tccaagtcca catgaactct gccaaggagt     360
agttggtttt acttacaaat tttggttatc tttataaaca ttttgtaagg tgtaggattt     420
gtgtgataac attttgatta gttaggctaa aaattgtatg tgctgagcta cgataccttc     480
tttctggtag aaagctacga tacctttaac cagaaaagga tccaaagaaa cgaacgaaac     540
caaactaggg gctaactcca aagtaggcga agctagaaaa gactcgactt ctctgtaccc     600
cagaagattg caaggcaatt tctctccaca aaaacaaaag aaccacgaag caaacaaagc     660
aaaaccaagc aaatttcctt ccaatttgcg tcaccgggtt atctccacgc attagaattt     720
tgaatcgatc tccatcaaac gtcacgacag acaaagaaga cgacttgact agcactgtac     780
caagaatgtg tgacgtggca gcttgcgtgt gccagcggta tggtcttcag ccaggaagaa     840
aaagagggag atatgacaag agaggcttgt gggaaatcac acacccatta ttgagattcc     900
ttccggatta ttcgtctaga ggcgtgtgca cggcgctgag aagcgtgtgg gctctgcgaa     960
ttaccaagct agcctctcat ggccaagtaa atgcctataa atgcccatcg cctccgccct    1020
tcctcaacaa cgtattgggt gatcgaatct atcagagtta caaacattgt ctctggtttc    1080
ctgcttcgaa actcaaaaca tgtcgacctg cggcaactgc gattgtgctg acaagagcca    1140
```

<210> SEQ ID NO 2
<211> LENGTH: 490
<212> TYPE: DNA
<213> ORGANISM: Elaeis sp.
<220> FEATURE:
<221> NAME/KEY: CDS
<222> LOCATION: (38)..(232)

<400> SEQUENCE: 2

```
aacattgtct ttggtttcct gcttcgaaac tcaaaac atg tcg acc tgc ggc aac      55
                                        Met Ser Thr Cys Gly Asn
                                         1               5
```

```
tgc gat tgt gct gac aag agc cag tgt gtg aag aag gga aac agc tac        103
Cys Asp Cys Ala Asp Lys Ser Gln Cys Val Lys Lys Gly Asn Ser Tyr
         10                  15                  20 ggc atc gag atc atc gag acc gaa aag agc aac ttc aac aat gtc atc        151
Gly Ile Glu Ile Ile Glu Thr Glu Lys Ser Asn Phe Asn Asn Val Ile
             25                  30                  35 gat gcc ccg gct gct gct gag cac gag ggc aac tgc aag tgt ggt gct        199
Asp Ala Pro Ala Ala Ala Glu His Glu Gly Asn Cys Lys Cys Gly Ala
 40                  45                  50 agc tgt gct tgt gtg gat tgc aag tgt ggc caa tgagcaacat ctatgagcac      252
Ser Cys Ala Cys Val Asp Cys Lys Cys Gly Gln
 55                  60                  65 tatagcaaac aagaaagaa agagatatgt gtgatatggg tatgttggac taaataattt       312
ggatatgttt ctgtcatggt gtgttattgt agcaaggatg tgtgtctgtc atggtgtgtt      372
attgttgtaa ggttggagga agacaatatc tgggcttcct tatccagttt cgcactaatt      432
tctattaacc tggttctaat taatggattg ctattggtag aaaaaaaaaa aaaaaaa        490

<210> SEQ ID NO 3
<211> LENGTH: 192
<212> TYPE: DNA
<213> ORGANISM: Elaeis sp.
<220> FEATURE:
<221> NAME/KEY: CDS
<222> LOCATION: (1)..(189)

<400> SEQUENCE: 3 atg tcg acc tgc ggc gac tgc gac tgc gct gac aag agc cag tgc gtg        48
Met Ser Thr Cys Gly Asp Cys Asp Cys Ala Asp Lys Ser Gln Cys Val
 1               5                  10                  15 aag aag gga aat ggt tac ggc atg gtc atc atc gag act gaa aag agc        96
Lys Lys Gly Asn Gly Tyr Gly Met Val Ile Ile Glu Thr Glu Lys Ser
             20                  25                  30 tac ttc gag gaa gtc gtt gag gtg gca gca gcc gcg gag cct gac tgc       144
Tyr Phe Glu Glu Val Val Glu Val Ala Ala Ala Ala Glu Pro Asp Cys
         35                  40                  45 aaa tgc ggc tct aac tgc gcc tgc gct ggt tgc acc tgt ggc aaa tga       192
Lys Cys Gly Ser Asn Cys Ala Cys Ala Gly Cys Thr Cys Gly Lys
 50                  55                  60

<210> SEQ ID NO 4
<211> LENGTH: 3936
<212> TYPE: DNA
<213> ORGANISM: Elaeis sp.

<400> SEQUENCE: 4
tggactcagt tcagaactaa taccaaaatg agccaacgtt gaggtagctg atgaaggaga       60
aatttcggac gcttttgatg ttcagctaga aaaatcttac tagtaaagag gggaaaacca     120
aaatcggcaa ccttttttt ttggtagaaa aatcagcaac ctttcaataa agagttttaa      180
tcctgtaaaa tatcaagtct agcaaattac caaagtaaag tgttgaaaaa aattaaaaaa     240 aaaaaaggg aatccgatct tccacaacct tatagcattc cagctaatgc ggctatccaa      300
aataagatgg atgggatgca ccagtcattc tgatgtgctt agaatttcca tcaaactcta     360
tcgtgcaact tgtgatttga caattcgag gtcgatgggg cagtgtcacc tttcatcatg      420
cacgcaagaa tccggggccc ttgcgagagt atttgcatgt taagcaaacg ttaaaaataa      480
agggatttga catcagaagc tcatagcccc ctaccaaaa aagagagag agaaacttca       540 accctccatt attgagattc catttggata gttttggtcg aggcgtgtgc cgccactgta      600
```

```
gcgtcagtaa tccgtttaag cccaccctcg cttttcctcat ccttgaaaac gcctataaat    660
atgggcggca cccaagcctc tttcctcaca gccagaccca gcaaaccttc tctcgagtca    720
cctgccatcc cttcgtccct cctctccttt tagcgacgc accatgtcga cctgcggcga    780
ctgcgactgc gctgacaaga gccagtgcgt gtaagtagtc cctcaccttg gaagctctcg    840
ctaacgcata gcagtcatgt tgcaaaactt atggttttta ctactaccag tcatcttgag    900
gagaaattat tagatggacc atgatgcatc atggatctaa aatgaaataa atcattttt    960
tcttttttcct tatatgtaat agcagcatgt attagaatga tttcaccctta ggtccattgg   1020
gatctagtcc acctaattaa taatttctcc atatttgcct ttggccttttg gtcatgatga   1080
ctggcatgtt tacaaattca gcatctctat tttactatct agaagatttt tcttatcaaa   1140
tgatcaatat tttaagtttt taatttcaac taagtagtta atgttgtggg gggttctggc   1200
ttatatggaa tgcgatcttt ttttttctcat gagtcgtctt ttaaaggaca aaattataaa   1260
gccctgtgcc ataagtcaga gaccgaagtg gacaatatct catgcatgtt ggagtggaga   1320
ctgatccatc caagtcatga gcccttgacc gcaacattcg tgtcatctgt gagataccaa   1380
tattgtgggg gattctggct tatatgaaat gtgatcttct ttttctcatg aggcgccttta   1440
taaaaagcaa aactgtgaag ccctatgtca taagccagag gtcaaaatgg acaatatctc   1500
atatatgtta gagtgaagac tgatctatcc gagtcatgag ctcttgaccg caatattcat   1560
gttatttgtg ggataccgtc tcctactcac acacagcact ccttttttgat tgggaggcta   1620
atattgtggg ggaaaaacgt attattagtc ccatatcgat tgtgagttaa gagaaaatct   1680
ggtttatatg gaatgggacc ttctctcttc cgtgagatgc tttttaaagg acaaaactgt   1740
aagatcccat gccatgagct agagatcgaa gtggataata cctcacacat gcaggagcgg   1800
agaccgatcc attccaacca caaatctttg accacaacgc ttagaagtga ttttatcagc   1860
ctctctcttg ctgtaggtaa ataatacatg taacaaattt caaacctcct aagtatacca   1920
catcagagtt tgatactaac ttttgtggtg catgcttact aaatagtcta actagatgag   1980
ggtacttcta ttatttttat gtcatctact aaactttatt gcccattctg atctaaatgg   2040
tttagaggag gtggtgtaac tttaaattttt ggaattttgg cacataaacc cacgtaaaac   2100
cgcactgacc tgggggtagaa cttttaaaatc actagaatga agggggggaa aaacaaaaga   2160
acttgtgtta gctagcttct atttatatat ttttctcata agaaaagctc actaagctaa   2220
cgaatctatt tgacgactgc aggaagaagg gaaatggtta cggcatggtc atcatcgaga   2280
ctgaaaagag gtatcaatca gatccaacaa gaaaataata ataacaatta aaaaaagaca   2340
ttttgtgccc atcggtgtat ggtatgcatg tacatacgta cgtatatatg tatacatata   2400
tgtgtgcata ttagtagaag atattaataa aaaaacactc aaatttggct catgatgcac   2460
agaaacctgt tctaaagttt ttttctttat tttttttttt ttttttttttg ttgggttggg   2520
ggcggcgggg tgggtaccc taaagacttt atttcagggc aattcctaat gtattggact   2580
gaatcatttg ttgcagctac ttcgaggaag tcgttgaggt ggcagcagcc gcggagcctg   2640
actgcaaatg cggctctaac tgcgcctgcg ctggttgcac ctgtggcaaa tgatagccta   2700
tctgctataa ttgttactat gtaagcaagg gaagataaaa tgacactagg gtttggttgt   2760
ggcaagtgat gtaggagtgc cattctatgt agtggtacca aggctgggag taagctgatg   2820
tccagctatc tcaacctaag taatatgtct gtgtcctatc ctgtttaacg gacttgtact   2880
aaaataaaat ctggctttgg tttgagtagt gatttctatg tcttttccac agtgtgaagt   2940
tttttttttt ttttgagtaa aataatgtga agtggtggtg ctgcattttta accttacatg   3000
```

-continued

```
ctccaggagc aactaaatct aagtagtagg tgcaaactga gcttagccca aagatttcac    3060
ctctcatatt tgggatctgg gagatcctgt cttcagtaca ccttgacatg agtactttca    3120 ttatttgtt cccactatgc tcaaaagata atatagacat atgcacacat acatatacaa    3180
atacatacat atataccta catatatac acatgtacca tgtggcacaa ggggattagt    3240
gtgtcgtaga gacctgacgg aatacctgta ctacaagagt tccaacctag tacgctggcc    3300
ttagaataaa agagcactca atctcatggg attccgcttg gtgttttaa tctacctttc    3360 ttcgtgacca actcccacgg atggtaatac gatgtatcag atcaaagatc cattgctcca    3420
accatgcgaa ccatcaacca ctgaccctgc caactgtaat tcacgttatg aaatactatt    3480
tgcctcaatc atgcgagtac cttttttcg gttcgtgata ttttaagaa gatatttagt    3540 ttgtgtagga atgagaatga gaattaaaat gatttggaat cgaaatcgga atagtcaaat    3600
cctacaaaat gtttgatttg tgaccggaat cgaaatcaga attggaataa aaattttgaat    3660 ccatagaaac gagtagggat tgaattccat atagattgag ccatttccat tccacctgta    3720
atcggaatca gaatcggaat gagaatcttt ctaaccaaac agctggaatg gaagtcaccc    3780
atttcgattc cgatttcaga cctccattct ctccaactaa acacccctta agttctttgc    3840
tttctatttc ctcactcttc atcataaagt atagtatttt cgcattgctt tcgttctta    3900 ttttcatttt caagaacgaa tcaaggacaa gattga                              3936
```

<210> SEQ ID NO 5
<211> LENGTH: 367
<212> TYPE: DNA
<213> ORGANISM: Elaeis sp.

<400> SEQUENCE: 5

```
aacgtattgg gtgatcgaat ctatcagagt tacaaacatt gtctttggtt tcctgcttcg      60
aaactcaaaa catgtcgacc tgcggcaact gcgattgtgc tgacaagagc cagtgtgtga     120
agaagggaaa cagctacggc atcgagatca tcgagaccga aaagagcaac ttcaacaatg     180
tcatcgatgc cccggctgct gctgagcacg agggcaactg caagtgtggt gctagctgtg     240
cttgtgtgga ttgcaagtgt ggccaatgag caacatctat gagcactata gcaaacaaga     300
aaagaaagag atatgtgtga tatgggtatg ttggactaaa taatttggat atgtttctgt     360
catggtg                                                              367
```

<210> SEQ ID NO 6
<211> LENGTH: 65
<212> TYPE: PRT
<213> ORGANISM: Elaeis sp.

<400> SEQUENCE: 6

```
Met Ser Thr Cys Gly Asn Cys Asp Cys Ala Asp Lys Ser Gln Cys Val
1               5                   10                  15

Lys Lys Gly Asn Ser Tyr Gly Ile Glu Ile Ile Glu Thr Glu Lys Ser
            20                  25                  30

Asn Phe Asn Asn Val Ile Asp Ala Pro Ala Ala Glu His Glu Gly
        35                  40                  45

Asn Cys Lys Cys Gly Ala Ser Cys Ala Cys Val Asp Cys Lys Cys Gly
    50                  55                  60

Gln
65
```

<210> SEQ ID NO 7
<211> LENGTH: 63
<212> TYPE: PRT
<213> ORGANISM: Elaeis sp.

<400> SEQUENCE: 7

Met Ser Thr Cys Gly Asp Cys Asp Cys Ala Asp Lys Ser Gln Cys Val
1               5                   10                  15

Lys Lys Gly Asn Gly Tyr Gly Met Val Ile Ile Glu Thr Glu Lys Ser
            20                  25                  30

Tyr Phe Glu Glu Val Val Glu Val Ala Ala Ala Ala Glu Pro Asp Cys
        35                  40                  45

Lys Cys Gly Ser Asn Cys Ala Cys Ala Gly Cys Thr Cys Gly Lys
    50                  55                  60

<210> SEQ ID NO 8
<211> LENGTH: 21
<212> TYPE: DNA
<213> ORGANISM: Elais sp.

<400> SEQUENCE: 8
ctaccaatag caatccatta a                                           21

<210> SEQ ID NO 9
<211> LENGTH: 16
<212> TYPE: DNA
<213> ORGANISM: Artificial Sequence
<220> FEATURE:
<223> OTHER INFORMATION: PCR primer

<400> SEQUENCE: 9 cttcccccccc cccccc                                                16

<210> SEQ ID NO 10
<211> LENGTH: 20
<212> TYPE: DNA
<213> ORGANISM: Elaeis sp.

<400> SEQUENCE: 10
caccatgaca gaaacatatc                                             20

<210> SEQ ID NO 11
<211> LENGTH: 29
<212> TYPE: DNA
<213> ORGANISM: Elaeis sp.

<400> SEQUENCE: 11
ccacacaagc acagctagca ccacacttg                                   29

<210> SEQ ID NO 12
<211> LENGTH: 29
<212> TYPE: DNA
<213> ORGANISM: Elaeis sp.

<400> SEQUENCE: 12
ctggctcttg tcagcacaat cgcagttgc                                   29

<210> SEQ ID NO 13
<211> LENGTH: 23
<212> TYPE: DNA
<213> ORGANISM: Artificial Sequence
<220> FEATURE:
<223> OTHER INFORMATION: PCR primer -continued

<400> SEQUENCE: 13
cccaagctta aattactgcc atg                                              23

<210> SEQ ID NO 14
<211> LENGTH: 25
<212> TYPE: DNA
<213> ORGANISM: Artificial Sequence
<220> FEATURE:
<223> OTHER INFORMATION: PCR primer

<400> SEQUENCE: 14
aaaactgcag caggaaacca gagac                                            25

<210> SEQ ID NO 15
<211> LENGTH: 24
<212> TYPE: DNA
<213> ORGANISM: Artificial Sequence
<220> FEATURE:
<223> OTHER INFORMATION: PCR primer

<400> SEQUENCE: 15
tgctctagac aggaaaccag agac                                             24

<210> SEQ ID NO 16
<211> LENGTH: 75
<212> TYPE: PRT
<213> ORGANISM: Pisum sativum

<400> SEQUENCE: 16

Met Ser Gly Cys Gly Cys Gly Ser Ser Cys Asn Cys Gly Asp Ser Cys
1               5                   10                  15
Lys Cys Asn Lys Arg Ser Ser Gly Leu Ser Tyr Ser Glu Met Glu Thr
            20                  25                  30
Thr Glu Thr Val Ile Leu Gly Val Gly Pro Ala Lys Ile Gln Phe Glu
        35                  40                  45
Gly Ala Glu Met Ser Ala Ala Ser Glu Asp Gly Gly Cys Lys Cys Gly
    50                  55                  60
Asp Asn Cys Thr Cys Asp Pro Cys Asn Cys Lys
65                  70                  75

<210> SEQ ID NO 17
<211> LENGTH: 76
<212> TYPE: PRT
<213> ORGANISM: Zea mays

<400> SEQUENCE: 17

Met Ser Cys Ser Cys Gly Ser Ser Cys Gly Cys Gly Ser Ser Cys Lys
1               5                   10                  15
Cys Gly Lys Lys Tyr Pro Asp Leu Glu Glu Thr Ser Thr Ala Ala Gln
            20                  25                  30
Pro Thr Val Val Leu Gly Val Ala Pro Glu Lys Lys Ala Ala Pro Glu
        35                  40                  45
Phe Val Glu Ala Ala Ala Glu Ser Gly Glu Ala Ala His Gly Cys Ser
    50                  55                  60
Cys Gly Ser Gly Cys Lys Cys Asp Pro Cys Asn Cys
65                  70                  75

<210> SEQ ID NO 18
<211> LENGTH: 75
<212> TYPE: PRT
<213> ORGANISM: Trifolium repens

<400> SEQUENCE: 18

Met Ser Gly Cys Asn Cys Gly Ser Ser Cys Asn Cys Gly Asp Ser Cys
1               5                   10                  15

Lys Cys Asn Lys Arg Ser Ser Gly Leu Asn Tyr Val Glu Ala Glu Thr
            20                  25                  30

Thr Glu Thr Val Ile Leu Gly Val Gly Pro Ala Lys Ile Gln Phe Glu
        35                  40                  45

Asp Ala Glu Met Gly Val Ala Ala Glu Asp Ser Gly Cys Lys Cys Gly
    50                  55                  60

Ser Ser Cys Thr Cys Asp Pro Cys Asn Cys Lys
65                  70                  75

<210> SEQ ID NO 19
<211> LENGTH: 74
<212> TYPE: PRT
<213> ORGANISM: Oryza sativa

<400> SEQUENCE: 19

Met Ser Cys Ser Cys Gly Ser Ser Cys Ser Cys Gly Ser Asn Cys Ser
1               5                   10                  15

Cys Gly Lys Lys Tyr Pro Asp Leu Glu Glu Lys Ser Ser Ser Thr Lys
            20                  25                  30

Ala Thr Val Val Leu Gly Val Ala Pro Glu Lys Lys Ala Gln Gln Phe
        35                  40                  45

Glu Ala Ala Ala Glu Ser Gly Glu Thr Ala His Gly Cys Ser Cys Gly
    50                  55                  60

Ser Ser Cys Arg Cys Asn Pro Cys Asn Cys
65                  70

<210> SEQ ID NO 20
<211> LENGTH: 82
<212> TYPE: PRT
<213> ORGANISM: Oryza sativa
<220> FEATURE:
<221> NAME/KEY: misc_feature
<222> LOCATION: (60)..(60)
<223> OTHER INFORMATION: Xaa can be any naturally occurring amino acid

<400> SEQUENCE: 20

Met Ser Cys Cys Gly Gly Asn Cys Gly Cys Gly Ser Gly Cys Gln Cys
1               5                   10                  15

Gly Ser Gly Cys Gly Gly Cys Lys Met Tyr Pro Glu Met Ala Glu Glu
            20                  25                  30

Val Thr Thr Thr Gln Thr Val Ile Met Gly Val Ala Pro Ser Lys Gly
        35                  40                  45

His Ala Glu Gly Leu Glu Ala Gly Ala Ala Xaa Ala Gly Ala Glu
    50                  55                  60

Asn Gly Cys Lys Cys Gly Asp Asn Cys Thr Cys Asn Pro Cys Asn Cys
65                  70                  75                  80

Gly Lys

<210> SEQ ID NO 21
<211> LENGTH: 81
<212> TYPE: PRT
<213> ORGANISM: Arabidopsis thaliana

<400> SEQUENCE: 21

Met Ser Cys Cys Gly Gly Asn Cys Gly Cys Gly Ser Gly Cys Lys Cys

```
                 1               5                  10                 15
Gly Asn Gly Cys Gly Gly Cys Lys Met Tyr Pro Asp Leu Gly Phe Ser
            20                  25                 30

Gly Glu Thr Thr Thr Thr Glu Thr Phe Val Leu Gly Val Ala Pro Ala
            35                  40                 45

Met Lys Asn Gln Tyr Glu Ala Ser Gly Glu Ser Asn Ala Glu Asn
            50                  55                 60

Asp Ala Cys Lys Cys Gly Ser Asp Cys Lys Cys Asp Pro Cys Thr Cys
65                  70                  75                 80

Lys

<210> SEQ ID NO 22
<211> LENGTH: 80
<212> TYPE: PRT
<213> ORGANISM: Ricinus communis

<400> SEQUENCE: 22

Met Ser Cys Cys Gly Gly Asn Cys Gly Cys Gly Ser Gly Cys Lys Cys
1               5                  10                 15

Gly Asn Gly Cys Gly Gly Cys Lys Met Tyr Pro Asp Met Ser Phe Ser
            20                  25                 30

Glu Lys Thr Thr Thr Glu Thr Leu Val Leu Gly Val Gly Ala Glu Lys
            35                  40                 45

Ala His Phe Glu Gly Gly Glu Met Gly Val Val Gly Ala Glu Glu Gly
            50                  55                 60

Gly Cys Lys Cys Gly Asp Asn Cys Thr Cys Asn Pro Cys Thr Cys Lys
65                  70                  75                 80

<210> SEQ ID NO 23
<211> LENGTH: 78
<212> TYPE: PRT
<213> ORGANISM: Actinidia deliciosa

<400> SEQUENCE: 23

Met Ser Cys Cys Gly Gly Lys Cys Gly Cys Gly Ser Ser Cys Ser Cys
1               5                  10                 15

Gly Ser Gly Cys Gly Gly Cys Gly Met Tyr Pro Asp Leu Ser Tyr Ser
            20                  25                 30

Glu Met Thr Thr Thr Glu Thr Leu Ile Val Gly Val Ala Pro Gln Lys
            35                  40                 45

Thr Tyr Phe Glu Gly Ser Glu Met Gly Val Ala Ala Glu Asn Gly Cys
            50                  55                 60

Lys Cys Gly Ser Asp Cys Lys Cys Asp Pro Cys Thr Cys Lys
65                  70                  75

<210> SEQ ID NO 24
<211> LENGTH: 63
<212> TYPE: PRT
<213> ORGANISM: Actinidia deliciosa

<400> SEQUENCE: 24

Met Ser Asp Lys Cys Gly Asn Cys Asp Cys Ala Asp Ser Ser Gln Cys
1               5                  10                 15

Val Lys Lys Gly Asn Ser Ile Asp Ile Val Glu Thr Asp Lys Ser Tyr
            20                  25                 30

Ile Glu Asp Val Val Met Gly Val Pro Ala Ala Glu Ser Gly Gly Lys
            35                  40                 45
```

```
Cys Lys Cys Gly Thr Ser Cys Pro Cys Val Asn Cys Thr Cys Asp
 50                  55                  60
```

<210> SEQ ID NO 25
<211> LENGTH: 65
<212> TYPE: PRT
<213> ORGANISM: Musa acuminata

<400> SEQUENCE: 25

```
Met Ser Thr Cys Gly Asn Cys Asp Cys Val Asp Lys Ser Gln Cys Val
 1               5                  10                  15

Lys Lys Gly Asn Ser Tyr Gly Ile Asp Ile Val Glu Thr Glu Lys Ser
             20                  25                  30

Tyr Val Asp Glu Val Ile Val Ala Ala Glu Ala Ala Glu His Asp Gly
         35                  40                  45

Lys Cys Lys Cys Gly Ala Ala Cys Ala Cys Thr Asp Cys Lys Cys Gly
 50                  55                  60

Asn
65
```

<210> SEQ ID NO 26
<211> LENGTH: 65
<212> TYPE: PRT
<213> ORGANISM: Carica papaya

<400> SEQUENCE: 26

```
Met Ser Asp Thr Cys Gly Asn Cys Asp Cys Ala Asp Lys Thr Gln Cys
 1               5                  10                  15

Val Lys Lys Gly Ser Ser Tyr Thr Ala Asp Ile Ile Glu Thr Glu Lys
             20                  25                  30

Ser Ile Met Thr Val Val Met Asp Ala Pro Ala Ala Glu Asn Asp Gly
         35                  40                  45

Lys Cys Lys Cys Gly Pro Ser Cys Ser Cys Thr Asn Cys Thr Cys Gly
 50                  55                  60

His
65
```

<210> SEQ ID NO 27
<211> LENGTH: 141
<212> TYPE: DNA
<213> ORGANISM: Elaeis sp.

<400> SEQUENCE: 27

```
atgcccatcg cctccgccct tcctcaacaa cgtattgggt gatcgaatct atcagagtta     60
caaacattgt ctttggtttc ctgcttcgaa actcaaaaca tgtcgacctg cggcaactgc    120
gattgtgctg acaagagcca g                                              141
```

<210> SEQ ID NO 28
<211> LENGTH: 158
<212> TYPE: DNA
<213> ORGANISM: Elais sp.
<220> FEATURE:
<221> NAME/KEY: misc_feature
<222> LOCATION: (1)..(28)
<223> OTHER INFORMATION: n is a, c, g, or t
<220> FEATURE:
<221> NAME/KEY: misc_feature
<222> LOCATION: (142)..(158)
<223> OTHER INFORMATION: n is a, c, g, or t

<400> SEQUENCE: 28

```
nnnnnnnnnn nnnnnnnnnn nnnnnnnnaa cgtattgggt gatcgaatct atcagagtta        60
caaacattgt ctttggtttc ctgcttcgaa actcaaaaca tgtcgacctg cggcaactgc       120
gattgtgctg acaagagcca gnnnnnnnnn nnnnnnnn                              158
```